US011065459B2

(12) United States Patent
Maile et al.

(10) Patent No.: US 11,065,459 B2
(45) Date of Patent: Jul. 20, 2021

(54) IMPLANTABLE MEDICAL DEVICE WITH PRESSURE SENSOR

(71) Applicant: CARDIAC PACEMAKERS, INC., St. Paul, MN (US)

(72) Inventors: Keith R. Maile, New Brighton, MN (US); William J. Linder, Golden Valley, MN (US); Moira B. Sweeney, St. Paul, MN (US); Michael J. Kane, St. Paul, MN (US); Brendan Early Koop, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 237 days.

(21) Appl. No.: 16/104,370

(22) Filed: Aug. 17, 2018

(65) Prior Publication Data

US 2019/0054304 A1    Feb. 21, 2019

Related U.S. Application Data

(60) Provisional application No. 62/547,458, filed on Aug. 18, 2017.

(51) Int. Cl.
*A61N 1/375* (2006.01)
*A61B 5/00* (2006.01)
(Continued)

(52) U.S. Cl.
CPC ........ *A61N 1/3756* (2013.01); *A61B 5/02158* (2013.01); *A61B 5/283* (2021.01);
(Continued)

(58) Field of Classification Search
CPC   A61N 1/3756; A61N 1/36564; A61B 5/0452; A61B 5/6869
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — William J Levicky
(74) *Attorney, Agent, or Firm* — Seager, Tufte & Wickhem LLP

(57) ABSTRACT

An implantable medical device (IMD) is configured with a pressure sensor. The IMD includes a housing and a diaphragm that is exposed to the environment outside of the housing. The diaphragm is configured to transmit a pressure from the environment outside of the housing to a piezoelectric membrane. In response, the piezoelectric membrane generates a voltage and/or a current, which is representative of a pressure change applied to the housing diaphragm. In some cases, only changes in pressure over time are used, not absolute or gauge pressures.

21 Claims, 16 Drawing Sheets

(51) Int. Cl.
    *A61N 1/365*     (2006.01)
    *A61B 5/0215*     (2006.01)
    *A61B 5/283*     (2021.01)
    *A61B 5/287*     (2021.01)
    *A61B 5/349*     (2021.01)
    *A61B 5/363*     (2021.01)
    *A61N 1/37*     (2006.01)
    *A61N 1/372*     (2006.01)
    *A61B 5/11*     (2006.01)
    *A61N 1/362*     (2006.01)
    *A61N 1/368*     (2006.01)

(52) U.S. Cl.
    CPC .............. *A61B 5/287* (2021.01); *A61B 5/349* (2021.01); *A61B 5/363* (2021.01); *A61B 5/686* (2013.01); *A61B 5/6869* (2013.01); *A61N 1/3655* (2013.01); *A61N 1/36564* (2013.01); *A61N 1/3702* (2013.01); *A61N 1/37276* (2013.01); *A61N 1/37512* (2017.08); *A61B 5/0031* (2013.01); *A61B 5/0215* (2013.01); *A61B 5/1107* (2013.01); *A61B 5/4836* (2013.01); *A61B 2560/0219* (2013.01); *A61B 2560/0462* (2013.01); *A61B 2562/0247* (2013.01); *A61N 1/3627* (2013.01); *A61N 1/3682* (2013.01); *A61N 1/3684* (2013.01); *A61N 1/36571* (2013.01); *A61N 1/36578* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,535,752 A | 7/1996 | Lalperin et al. |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |

(56) References Cited

U.S. PATENT DOCUMENTS

| | | |
|---|---|---|
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,314,323 B1 | 11/2001 | Ekwall |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,088 B2 | 3/2005 | Chinchoy |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |

(56) References Cited

U.S. PATENT DOCUMENTS

| | | |
|---|---|---|
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,142,917 B2 | 11/2006 | Fukui |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,861 B1 | 5/2007 | Park et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,875 B1 | 10/2007 | Park et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,418,868 B1 | 9/2008 | Karicherla et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,580,746 B2 | 8/2009 | Gilkerson et al. |
| 7,584,002 B2 | 9/2009 | Burnes et al. |
| 7,590,455 B2 | 9/2009 | Heruth et al. |
| 7,596,412 B1 | 9/2009 | Kroll |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,763 B2 | 12/2009 | Kwok et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,676,266 B1 | 3/2010 | Kroll |
| 7,682,316 B2 | 3/2010 | Anderson et al. |
| 7,691,047 B2 | 4/2010 | Ferrari |
| 7,702,389 B2 | 4/2010 | Czygan et al. |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |

(56) References Cited

U.S. PATENT DOCUMENTS

| | | |
|---|---|---|
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,306,621 B2 | 11/2012 | Kim et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,400 B2 | 7/2013 | Hettrick et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,521,265 B2 | 7/2013 | Volkron et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |

(56) References Cited

U.S. PATENT DOCUMENTS

| | | |
|---|---|---|
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,721 B2 | 9/2014 | Hettrick et al. |
| 8,831,747 B1 | 9/2014 | Min et al. |
| 8,843,198 B2 | 9/2014 | Lian et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,479 B2 | 10/2015 | Solem |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,174,062 B2 | 11/2015 | Stadler et al. |
| 9,180,285 B2 | 11/2015 | Moore et al. |
| 9,192,774 B2 | 11/2015 | Jacobson |
| 9,199,086 B2 | 12/2015 | Zielinski et al. |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,954 B2 | 2/2016 | Ghosh |
| 9,265,955 B2 | 2/2016 | Ghosh |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |

(56) References Cited

U.S. PATENT DOCUMENTS

| | | |
|---|---|---|
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,201,710 B2 | 2/2019 | Jackson et al. |
| 10,207,115 B2 | 2/2019 | Echt et al. |
| 10,207,116 B2 | 2/2019 | Sheldon et al. |
| 10,226,197 B2 | 3/2019 | Reinke et al. |
| 10,226,639 B2 | 3/2019 | Zhang |
| 10,232,182 B2 | 3/2019 | Hareland et al. |
| 10,265,503 B2 | 4/2019 | Schmidt et al. |
| 10,265,534 B2 | 4/2019 | Greenhut et al. |
| 10,271,752 B2 | 4/2019 | Regnier et al. |
| 10,278,601 B2 | 5/2019 | Greenhut et al. |
| 10,279,165 B2 | 5/2019 | Seifert et al. |
| 10,286,221 B2 | 5/2019 | Sawchuk |
| 10,307,598 B2 | 6/2019 | Ciciarelli et al. |
| 10,328,274 B2 | 6/2019 | Zhang et al. |
| 10,342,981 B2 | 7/2019 | Ghosh et al. |
| 2001/0012953 A1 | 8/2001 | Molin et al. |
| 2001/0021864 A1 | 9/2001 | Molin |
| 2001/0031995 A1 | 10/2001 | Molin |
| 2001/0034540 A1 | 10/2001 | Molin |
| 2001/0049543 A1 | 12/2001 | Kroll |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0087089 A1 | 7/2002 | Ben Haim |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2003/0204212 A1 | 10/2003 | Burnes et al. |
| 2004/0024435 A1 | 2/2004 | Leckrone et al. |
| 2004/0032957 A1* | 2/2004 | Mansy ............... A61B 5/04085 381/67 |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0038481 A1 | 2/2005 | Chinchoy et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182447 A1 | 8/2005 | Schecter |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0041281 A1 | 2/2006 | Von Arx et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0247707 A1 | 11/2006 | Meyer et al. |
| 2006/0259088 A1 | 11/2006 | Pastore et al. |
| 2006/0265018 A1 | 11/2006 | Smith et al. |
| 2006/0271119 A1 | 11/2006 | Ni et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049977 A1* | 3/2007 | Von Arx ............... A61B 7/023 607/9 |
| 2007/0055170 A1 | 3/2007 | Lippert et al. |
| 2007/0060961 A1 | 3/2007 | Echt |

(56) References Cited

U.S. PATENT DOCUMENTS

| | | |
|---|---|---|
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0093874 A1* | 4/2007 | Chirife ............... A61N 1/368 607/25 |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0156194 A1 | 7/2007 | Wang |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0195167 A1 | 8/2008 | Ryan |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1* | 4/2009 | Brockway ............ A61N 1/0587 607/14 |
| 2009/0118783 A1 | 5/2009 | Pantangay et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171404 A1 | 7/2009 | Irani et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275843 A1 | 11/2009 | Karamanoglu |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069768 A1 | 3/2010 | Min et al. |
| 2010/0069983 A1 | 3/2010 | Peacock, III et al. |
| 2010/0094367 A1 | 4/2010 | Sen |
| 2010/0106213 A1 | 4/2010 | Hilpisch et al. |
| 2010/0113944 A1 | 5/2010 | Min et al. |
| 2010/0113945 A1 | 5/2010 | Ryan |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0305646 A1 | 12/2010 | Schulte et al. |
| 2010/0312309 A1 | 12/2010 | Harding |
| 2010/0317978 A1* | 12/2010 | Maile ................. A61B 5/0215 600/488 |
| 2010/0331905 A1 | 12/2010 | Li et al. |
| 2011/0022113 A1 | 1/2011 | Zdeblick et al. |
| 2011/0022127 A1 | 1/2011 | Averina et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0125208 A1 | 5/2011 | Karst et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160787 A1 | 6/2011 | Greenhut et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |

(56) References Cited

U.S. PATENT DOCUMENTS

| | | |
|---|---|---|
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0136406 A1 | 5/2012 | Min |
| 2012/0150251 A1 | 6/2012 | Giftakis et al. |
| 2012/0158111 A1 | 6/2012 | Khairkhahan et al. |
| 2012/0165692 A1 | 6/2012 | Hollmark et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2012/0330392 A1 | 12/2012 | Regnier et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079839 A1 | 3/2013 | Lian et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0213916 A1 | 7/2014 | Doan et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster |
| 2014/0277240 A1 | 9/2014 | Maskara et al. |
| 2014/0303704 A1 | 10/2014 | Suwito et al. |

(56) References Cited

U.S. PATENT DOCUMENTS

| | | |
|---|---|---|
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0091415 A1 | 4/2015 | Deterre et al. |
| 2015/0105836 A1 | 4/2015 | Bonner et al. |
| 2015/0126854 A1 | 5/2015 | Keast et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0157866 A1 | 6/2015 | Demmer et al. |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0202443 A1 | 7/2015 | Zielinski et al. |
| 2015/0217119 A1 | 8/2015 | Nikolski et al. |
| 2015/0217123 A1 | 8/2015 | Deterre et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2015/0360036 A1 | 12/2015 | Kane et al. |
| 2015/0367135 A1 | 12/2015 | Whittington et al. |
| 2016/0007873 A1 | 1/2016 | Huelskamp et al. |
| 2016/0015322 A1 | 1/2016 | Anderson et al. |
| 2016/0023000 A1* | 1/2016 | Cho ................ A61N 1/3682 607/18 |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0067486 A1 | 3/2016 | Brown et al. |
| 2016/0067490 A1 | 3/2016 | Carney et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129262 A1 | 5/2016 | Sheldon et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0256694 A1* | 9/2016 | Shuros ................ A61B 5/686 |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0310723 A1 | 10/2016 | Eggen et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112390 A1 | 4/2017 | Cho et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatan et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |
| 2018/0056079 A1 | 3/2018 | Hahn et al. |
| 2018/0078773 A1 | 3/2018 | Thakur et al. |
| 2018/0116593 A1 | 5/2018 | An et al. |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 2030564 A2 | 3/2009 |
| EP | 1904166 B1 | 6/2011 |
| EP | 2471449 A1 | 7/2012 |
| EP | 2471452 A1 | 7/2012 |
| EP | 2433675 B1 | 1/2013 |

(56) References Cited

FOREIGN PATENT DOCUMENTS

| | | | |
|---|---|---|---|
| EP | 2441491 | B1 | 1/2013 |
| EP | 2639845 | A1 | 9/2013 |
| EP | 2452721 | B1 | 11/2013 |
| EP | 2662113 | A3 | 11/2013 |
| EP | 1948296 | B1 | 1/2014 |
| EP | 2280759 | B1 | 5/2015 |
| EP | 2760541 | B1 | 5/2016 |
| EP | 2833966 | B1 | 5/2016 |
| JP | 2000051373 | A | 2/2000 |
| JP | 2002502640 | A | 1/2002 |
| JP | 2004512105 | A | 4/2004 |
| JP | 2005508208 | A | 3/2005 |
| JP | 2005245215 | A | 9/2005 |
| JP | 2008540040 | A | 11/2008 |
| JP | 5199867 | B2 | 2/2013 |
| WO | 9407567 | A1 | 4/1994 |
| WO | 9500202 | A1 | 1/1995 |
| WO | 9636134 | A1 | 11/1996 |
| WO | 9724981 | A2 | 7/1997 |
| WO | 9826840 | A1 | 6/1998 |
| WO | 9939767 | A1 | 8/1999 |
| WO | 0234330 | A2 | 5/2002 |
| WO | 02098282 | A2 | 12/2002 |
| WO | 2003051457 | A1 | 6/2003 |
| WO | 2004078254 | A2 | 9/2004 |
| WO | 2005000206 | A3 | 1/2005 |
| WO | 2005018740 | A1 | 3/2005 |
| WO | 2005042089 | A1 | 5/2005 |
| WO | 2006065394 | A1 | 6/2006 |
| WO | 2006069215 | A2 | 6/2006 |
| WO | 2006086435 | A3 | 8/2006 |
| WO | 2006113659 | A1 | 10/2006 |
| WO | 2006124833 | A3 | 11/2006 |
| WO | 2007073435 | A1 | 6/2007 |
| WO | 2007075974 | A2 | 7/2007 |
| WO | 2007033094 | A2 | 10/2007 |
| WO | 2008034005 | A2 | 3/2008 |
| WO | 2009006531 | A1 | 1/2009 |
| WO | 2009025734 | A1 | 2/2009 |
| WO | 2009131768 | A1 | 10/2009 |
| WO | 2010088687 | A1 | 8/2010 |
| WO | 2012054102 | A1 | 4/2012 |
| WO | 2013003754 | A1 | 1/2013 |
| WO | 2013080038 | A2 | 6/2013 |
| WO | 2013098644 | A3 | 7/2013 |
| WO | 2013184787 | A1 | 12/2013 |
| WO | 2014120769 | A1 | 8/2014 |
| WO | 2014178035 | A1 | 11/2014 |
| WO | 2016022397 | A1 | 2/2016 |
| WO | 2016118735 | A1 | 7/2016 |

OTHER PUBLICATIONS

International Search Report and Written Opinion dated Sep. 6, 2017 for International Application No. PCT/US2017/039726.
Liang, "Piezoelectric Pressure Sensors Based on Flexible PZT Thick Film Composite Device," University of Pittsburgh, 2014, 97 pages.
International Search Report and Written Opinion for Application No. PCT/US2017/057929, 12 pages, dated Jan. 26, 2018.
International Search Report and Written Opinion dated Oct. 5, 2017 for International Application No. PCT/US2017/037961.
International Search Report and Written Opinion for Application No. PCT/US2017/041562, 12 pages, dated Nov. 30, 2017.
Ginks et al; "Relationship between intracardiac impedance and left Ventricular contactility in patients undergoing cardiac resynchrinization," Europace, vol. 13, 984-991, 2001.
MPVS Ultra, "Complete PV Loop Analysis", Pressure-Volume Loop Systems, Millar, downloaded Nov. 2017.
Roest et al; Prediction of long-term outcome of cardiac resynchronization therapy by acute pressure-volume loop measurements, European Journal of Heart Failure, 15, 299-307, 2013.
"Complete PV Loop Analysis," Millar, pp. 1-4, 2014.
International Search Report and Written Opinion for Application No. PCT/US2018/046885, 22 pages, dated Nov. 15, 2018.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.

\* cited by examiner

IMPLANTABLE MEDICAL DEVICE WITH PRESSURE SENSOR

CROSS REFERENCE TO RELATED APPLICATIONS

This application claims the benefit of U.S. Provisional Patent Application Ser. No. 62/547,458 filed on Aug. 18, 2017, the disclosure of which is incorporated herein by reference.

TECHNICAL FIELD

The present disclosure generally relates to implantable medical devices and more particularly to implantable medical devices with pressure sensors

BACKGROUND

Implantable medical devices are commonly used to perform a variety of functions, such as to monitor one or more conditions and/or delivery therapy to a patient. In some cases, an implantable medical device may deliver neurostimulation therapy to a patient. In some cases, an implantable medical device may simply monitor one or more conditions, such as pressure, acceleration, cardiac events, and may communicate the detected conditions or events to another device, such as another implantable medical device or an external programmer.

In some cases, an implantable medical device may be configured to deliver pacing and/or defibrillation therapy to a patient. Such implantable medical devices may treat patients suffering from various heart conditions that may result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) may be implanted into a patient's body. When so provided, such devices can monitor and provide therapy, such as electrical stimulation therapy, to the patient's heart to help the heart operate in a more normal, efficient and/or safe manner. In some cases, a patient may have multiple implanted devices that cooperate to monitor and/or provide therapy to the patient's heart.

SUMMARY

The present disclosure generally relates to implantable medical devices and more particularly to implantable medical devices with pressure sensors.

In a first example, a leadless cardiac pacemaker (LCP) may be configured to sense cardiac activity and to deliver pacing therapy to a patient's heart. The LCP may comprise a housing having a proximal end and a distal end, a first electrode secured relative to the housing and exposed to the environment outside of the housing, a second electrode secured relative to the housing and exposed to the environment outside of the housing, a diaphragm that is exposed to the environment outside of the housing, the diaphragm is responsive to an external pressure applied to the diaphragm by the environment outside of the housing, a piezoelectric membrane having a first pressure sensor electrode and a second pressure sensor electrode, the piezoelectric membrane may be configured to generate an electrical voltage between the first pressure sensor electrode and the second pressure sensor electrode in response to a pressure change applied to the diaphragm, the electrical voltage representative of a change in external pressure applied to the diaphragm, and circuitry in the housing operatively coupled to the first electrode and the second electrode of the LCP, and also operatively coupled to the first pressure sensor electrode and the second pressure sensor electrode, the circuitry may be configured to deliver a pacing therapy to the patient's heart via the first electrode and the second electrode of the LCP, wherein the pacing therapy is dependent, at least in part, on the electrical voltage generated by the piezoelectric membrane and that is representative of the change in external pressure applied to the diaphragm.

Alternatively or additionally to any of the examples above, in another example, the circuitry may be configured to detect a pressure pulse by monitoring the electrical voltage generated between the first pressure sensor electrode and the second pressure sensor electrode by the piezoelectric membrane.

Alternatively or additionally to any of the examples above, in another example, the diaphragm may have an interior surface that faces toward an interior of the housing, and the piezoelectric may be secured to at least part of the interior surface of the diaphragm.

Alternatively or additionally to any of the examples above, in another example, the diaphragm may have an interior surface that faces toward an interior of the housing, and the piezoelectric membrane may be spaced a distance from the interior surface of the diaphragm and may be operatively coupled to the interior surface of the diaphragm via an incompressible fluid.

Alternatively or additionally to any of the examples above, in another example, the incompressible fluid may be in a fluid cavity that is at least partially defined by the interior surface of the diaphragm and may be in fluid communication with both the interior surface of the diaphragm and the piezoelectric membrane, wherein the fluid cavity may be configured to communicate a pressure applied to the incompressible fluid by the diaphragm to the piezoelectric membrane.

Alternatively or additionally to any of the examples above, in another example, the diaphragm may have an interior surface that faces toward an interior of the housing, and the piezoelectric membrane may be spaced a distance from the interior surface of the diaphragm and may be operatively coupled to the interior surface of the diaphragm via a mechanical linkage, wherein the mechanical linkage may be configured to translate movement of the diaphragm to a pressure applied to the piezoelectric membrane.

Alternatively or additionally to any of the examples above, in another example, the diaphragm of the housing may include one or more contours.

Alternatively or additionally to any of the examples above, in another example, the circuitry may be configured to detect a change in pressure in a first chamber of the heart caused by a contraction of a second chamber of the heart.

Alternatively or additionally to any of the examples above, in another example, the first chamber may be a ventricle, and the second chamber may be the corresponding atrium.

Alternatively or additionally to any of the examples above, in another example, the diaphragm may be integrally formed with the housing.

Alternatively or additionally to any of the examples above, in another example, the diaphragm may be hermetically sealed to the housing.

Alternatively or additionally to any of the examples above, in another example, the LCP may further comprise a fixation member at the distal end of the housing for fixing the distal end of the housing to an implant site, and wherein the diaphragm of the housing is adjacent the proximal end of the housing.

Alternatively or additionally to any of the examples above, in another example, the housing may include an elongated body with a distal end surface facing distally and a proximal end surface facing proximally, wherein the diaphragm of the housing may be situated on the proximal end surface of the housing.

Alternatively or additionally to any of the examples above, in another example, the diaphragm and/or piezoelectric membrane may be formed to maximize the dynamic change of the diaphragm and/or piezoelectric membrane when implanted.

Alternatively or additionally to any of the examples above, in another example, the LCP may further comprise an anti-thrombogenic coating disposed over the diaphragm of the housing.

In another example, a leadless cardiac pacemaker (LCP) may be configured to sense cardiac activity and to deliver pacing therapy to a patient's heart. The LCP may comprise a housing having a proximal end and a distal end, a first electrode secured relative to the housing and exposed to the environment outside of the housing, a second electrode secured relative to the housing and exposed to the environment outside of the housing, a diaphragm that is exposed to the environment outside of the housing, the diaphragm is responsive to an external pressure applied to the diaphragm by the environment outside of the housing, a piezoelectric membrane having a first pressure sensor electrode and a second pressure sensor electrode, the piezoelectric membrane may be configured to generate an electrical voltage between the first pressure sensor electrode and the second pressure sensor electrode in response to a pressure change applied to the diaphragm, the electrical voltage representative of a change in external pressure applied to the diaphragm, and circuitry in the housing operatively coupled to the first electrode and the second electrode of the LCP, and also operatively coupled to the first pressure sensor electrode and the second pressure sensor electrode, the circuitry may be configured to deliver a pacing therapy to the patient's heart via the first electrode and the second electrode of the LCP, wherein the pacing therapy is dependent, at least in part, on the electrical voltage generated by the piezoelectric membrane and that is representative of the change in external pressure applied to the diaphragm.

Alternatively or additionally to any of the examples above, in another example, the circuitry may be configured to detect a pressure pulse by monitoring the electrical voltage generated between the first pressure sensor electrode and the second pressure sensor electrode by the piezoelectric membrane.

Alternatively or additionally to any of the examples above, in another example, the diaphragm may have an interior surface that faces toward an interior of the housing, and the piezoelectric membrane may be secured to at least part of the interior surface of the diaphragm.

Alternatively or additionally to any of the examples above, in another example, the diaphragm may have an interior surface that faces toward an interior of the housing, and the piezoelectric membrane may be spaced a distance from the interior surface of the diaphragm and may be operatively coupled to the interior surface of the diaphragm via an incompressible fluid.

Alternatively or additionally to any of the examples above, in another example, the incompressible fluid may be in a fluid cavity that is at least partially defined by the interior surface of the diaphragm and may be in fluid communication with both the interior surface of the diaphragm and the piezoelectric membrane, wherein the fluid cavity may be configured to communicate a pressure applied to the incompressible fluid by the diaphragm to the piezoelectric membrane.

Alternatively or additionally to any of the examples above, in another example, the diaphragm may have an interior surface that faces toward an interior of the housing, and the piezoelectric membrane may be spaced a distance from the interior surface of the diaphragm and may be operatively coupled to the interior surface of the diaphragm via a mechanical linkage, wherein the mechanical linkage may be configured to translate movement of the diaphragm to a pressure applied to the piezoelectric membrane.

Alternatively or additionally to any of the examples above, in another example, the diaphragm of the housing may include one or more contours.

Alternatively or additionally to any of the examples above, in another example, the circuitry may be configured to detect a change in pressure in a first chamber of the heart caused by a contraction of a second chamber of the heart.

Alternatively or additionally to any of the examples above, in another example, the first chamber may be a ventricle, and the second chamber may be the corresponding atrium.

Alternatively or additionally to any of the examples above, in another example, the diaphragm may be integrally formed with the housing.

Alternatively or additionally to any of the examples above, in another example, the diaphragm may be hermetically sealed to the housing.

Alternatively or additionally to any of the examples above, in another example, the LCP may further comprise a fixation member at the distal end of the housing for fixing the distal end of the housing to an implant site, and wherein the diaphragm of the housing may be adjacent the proximal end of the housing.

Alternatively or additionally to any of the examples above, in another example, the housing may include an elongated body with a distal end surface facing distally and a proximal end surface facing proximally, wherein the diaphragm of the housing may be situated on the proximal end surface of the housing.

Alternatively or additionally to any of the examples above, in another example, the diaphragm and/or piezoelectric membrane may be formed to maximize the dynamic change of the diaphragm and/or piezoelectric membrane when implanted.

In another example, a leadless cardiac pacemaker (LCP) may be configured to sense cardiac activity and to pace a patient's heart. The LCP may comprise a housing having a proximal end and a distal end, a first electrode secured relative to the housing and exposed to the environment outside of the housing, a second electrode secured relative to the housing and exposed to the environment outside of the housing, the housing having a diaphragm that is exposed to the environment outside of the housing, the diaphragm is responsive to a pressure applied to the diaphragm by the environment outside of the housing, a piezoelectric material operatively coupled to the diaphragm of the housing for detecting a deflection in the diaphragm by generating charge that is representative of the pressure applied to the diaphragm by the environment outside of the housing, and circuitry in the housing in operative communication with the first electrode, the second electrode and the piezoelectric material, the circuitry may be configured to deliver a pacing therapy to the patient's heart via the first electrode and the second electrode, wherein the pacing therapy is dependent, at least in part, on the charge that is generated by the piezoelectric material and that is representative of the pressure applied to the diaphragm by the environment outside of the housing.

Alternatively or additionally to any of the examples above, in another example, the circuitry may be configured to detect a pressure pulse by monitoring the charge generated by the piezoelectric material.

Alternatively or additionally to any of the examples above, in another example, the circuitry may be configured to detect a change in pressure in a first chamber of the heart caused by a contraction of a second chamber of the heart.

Alternatively or additionally to any of the examples above, in another example, the first chamber may be a ventricle, and the second chamber may be the corresponding atrium.

In another example, an implantable medical device (IMD) may comprise a housing having a proximal end and a distal end, a first electrode secured relative to the housing and exposed to the environment outside of the housing, a second electrode secured relative to the housing and exposed to the environment outside of the housing, the housing having a diaphragm that is exposed to the environment outside of the housing, the diaphragm is responsive to a pressure applied to the diaphragm by the environment outside of the housing, a piezoelectric membrane disposed on an inner surface of the diaphragm, the piezoelectric membrane generating a charge in response to the pressure applied to the diaphragm by the environment outside of the housing, and circuitry in the housing in operative communication with the first electrode, the second electrode and the piezoelectric membrane, the circuitry may be configured to deliver an electrostimulation therapy to the patient's heart via the first electrode and the second electrode, wherein the therapy is dependent, at least in part, on the charge that is generated by the piezoelectric membrane and that is representative of the pressure applied to the diaphragm by the environment outside of the housing.

Alternatively or additionally to any of the examples above, in another example, the piezoelectric membrane may comprise polyvinylidene fluoride (PVDF).

Alternatively or additionally to any of the examples above, in another example, the circuitry may be configured to detect a change in pressure in a first chamber of a heart caused by a contraction of a second chamber of the heart.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
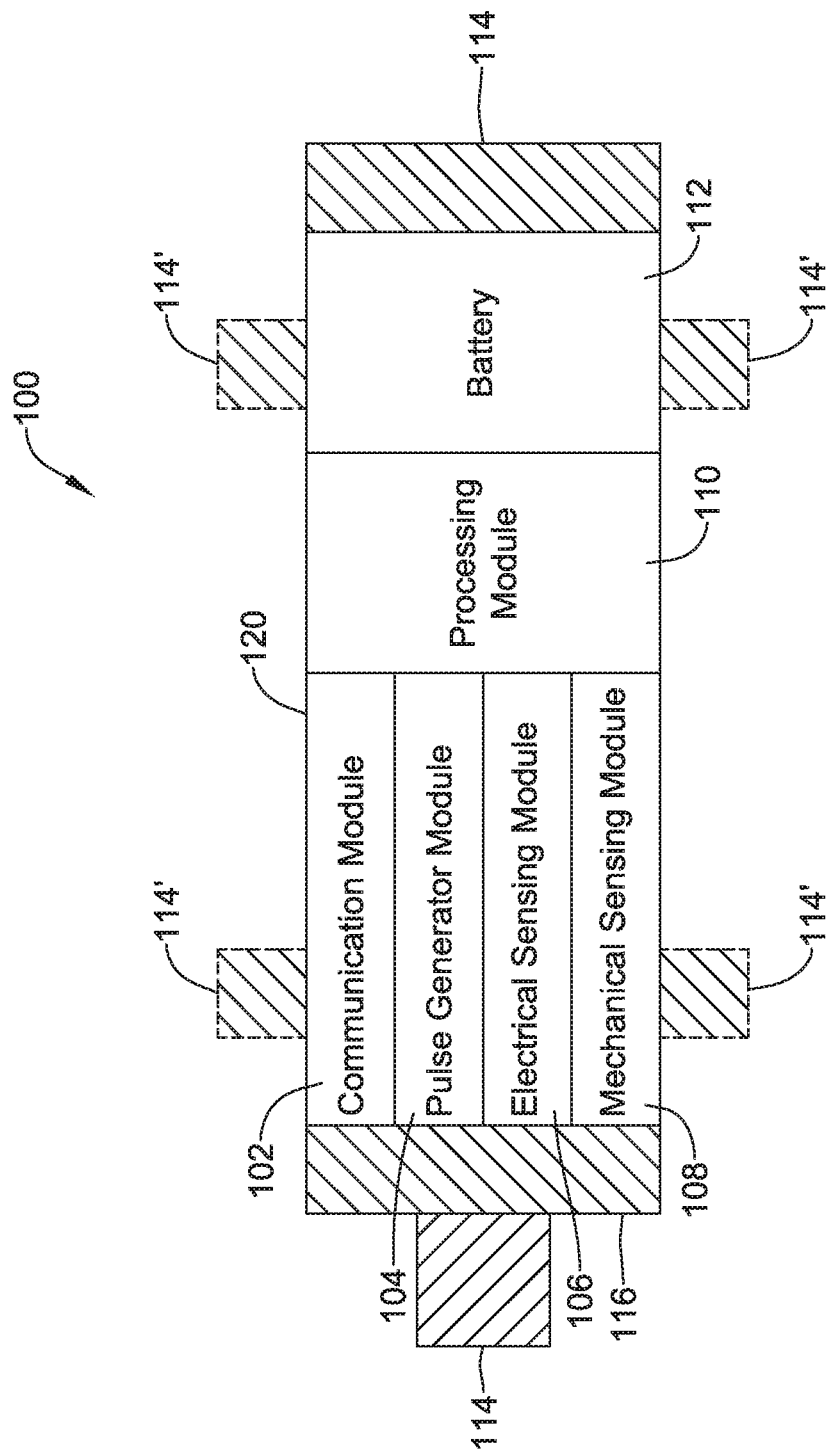
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure. While the present disclosure is applicable to any suitable implantable medical device (IMD), the description below uses pacemakers and more particularly leadless cardiac pacemakers (LCP) as particular examples.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may initiate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely desynchronized and the heart pumps very little to no blood. Implantable medical devices, which may be configured to determine occurrences of such cardiac abnormalities or arrhythmias and deliver one or more types of electrical stimulation therapy to patient's hearts, may help to terminate or alleviate these and other cardiac conditions.

FIG. 1 depicts an illustrative leadless cardiac pacemaker (LCP) that may be implanted into a patient and may operate to prevent, control, or terminate cardiac arrhythmias in patients by, for example, appropriately employing one or more therapies (e.g., anti-tachycardia pacing (ATP) therapy, cardiac resynchronization therapy (CRT), bradycardia therapy, defibrillation pulses, or the like). As can be seen in FIG. 1, the LCP 100 may be a compact device with all components housed within the LCP 100 or directly on the housing 120. In the example shown in FIG. 1, the LCP 100 may include a communication module 102, a pulse generator module 104, an electrical sensing module 106, a mechanical sensing module 108, a processing module 110, a battery 112, and electrodes 114. The LCP 100 may include more or less modules, depending on the application.

The communication module 102 may be configured to communicate with devices such as sensors, other medical devices, and/or the like, that are located externally to the LCP 100. Such devices may be located either external or internal to the patient's body. Irrespective of the location, remote devices (i.e., external to the LCP 100 but not necessarily external to the patient's body) can communicate with the LCP 100 via the communication module 102 to accomplish one or more desired functions. For example, the LCP 100 may communicate information, such as sensed electrical signals, data, instructions, messages, etc., to an external medical device through the communication module 102. The external medical device may use the communicated signals, data, instructions and/or messages to perform various functions, such as determining occurrences of arrhythmias, delivering electrical stimulation therapy, storing received data, analyzing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, analyzing received data, and/or performing any other suitable function. The communication module 102 may be configured to use one or more methods for communicating with remote devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, the LCP 100 may include one or more additional electrodes 114'. In such examples, the pulse generator 104 may also be electrically connected to the additional electrodes 114'. The pulse generator module 104 may be configured to generate electrical stimulation signals. For example, the pulse generator module 104 may generate electrical stimulation signals by using energy stored in a battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac dyssynchrony, bradycardia arrhythmias, tachycardia arrhythmias, fibrillation arrhythmias, cardiac synchronization arrhythmias and/or to produce any other suitable electrical stimulation therapy. Some more common electrical stimulation therapies include bradycardia therapy, anti-tachycardia pacing (ATP) therapy, cardiac resynchronization therapy (CRT), and cardioversion/defibrillation therapy.

In some examples, the LCP 100 may not include a pulse generator 104 or may turn off the pulse generator 104. When so provided, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart, cardiac electrical signals sensed by the LCP 100 through the electrodes 114/114' may represent ventricular cardiac electrical signals. The mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical and/or chemical parameters of the patient. Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to LCP 100 may have an insulative portion that electrically isolates the electrodes 114/114' from adjacent electrodes, the housing 120, and/or other parts of the LCP 100.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, occurrences and, in some cases, types of arrhythmias. Based on any determined arrhythmias, the processing module 110 may control the pulse generator module 104 to generate electrical stimulation in accordance with one or more therapies to treat the determined arrhythmia(s). The processing module 110 may further receive information from the communication module 102. In some examples, the processing module 110 may use such received information to help determine whether an arrhythmia is occurring, determine a type of arrhythmia, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g., general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
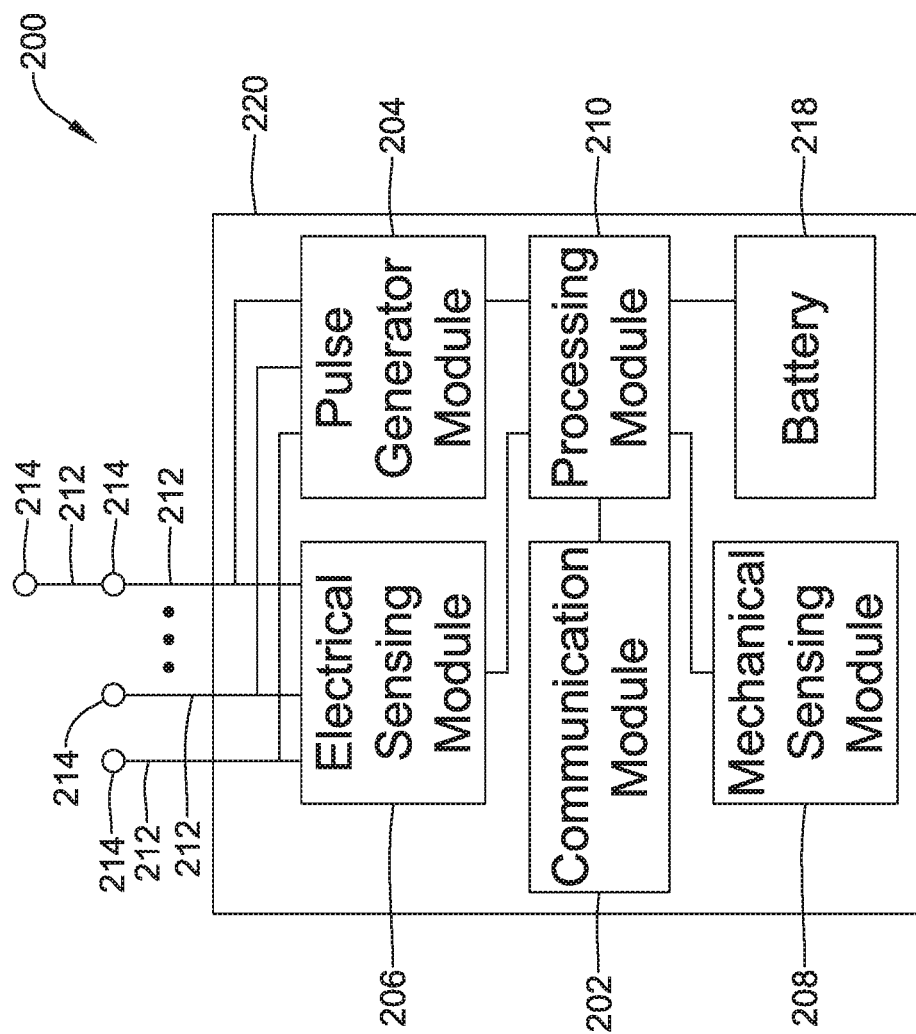
FIG. 2 is a schematic block diagram of another medical device (MD), which may be used in conjunction with an LCP 100 (FIG. 1) in order to detect and/or treat cardiac arrhythmias and other heart conditions.

FIG. 2 depicts an example of another medical device (MD) 200, which may be used in conjunction with an LCP 100 (FIG. 1) in order to detect and/or treat cardiac arrhythmias and other heart conditions. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some examples, the MD 200 may have a larger volume within the housing 220 than LCP 100. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some of the leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned substernally or subcutaneously but adjacent the patient's heart. In some cases, the electrodes 214 may conduct intrinsically generated electrical signals to the leads 212, e.g., signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, blood pressure sensors, heart sound sensors, blood-oxygen sensors, acoustic sensors, ultrasonic sensors and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart or in concert with the LCP by commanding the LCP to pace. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In some instances, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some cases, the S-ICD lead may extend subcutaneously from the S-ICD can, around the sternum and may terminate adjacent the interior surface of the sternum.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g., cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. The MD 200 may be further configured to deliver electrical stimulation via the LCP by commanding the LCP to deliver the therapy.

Figure 3:
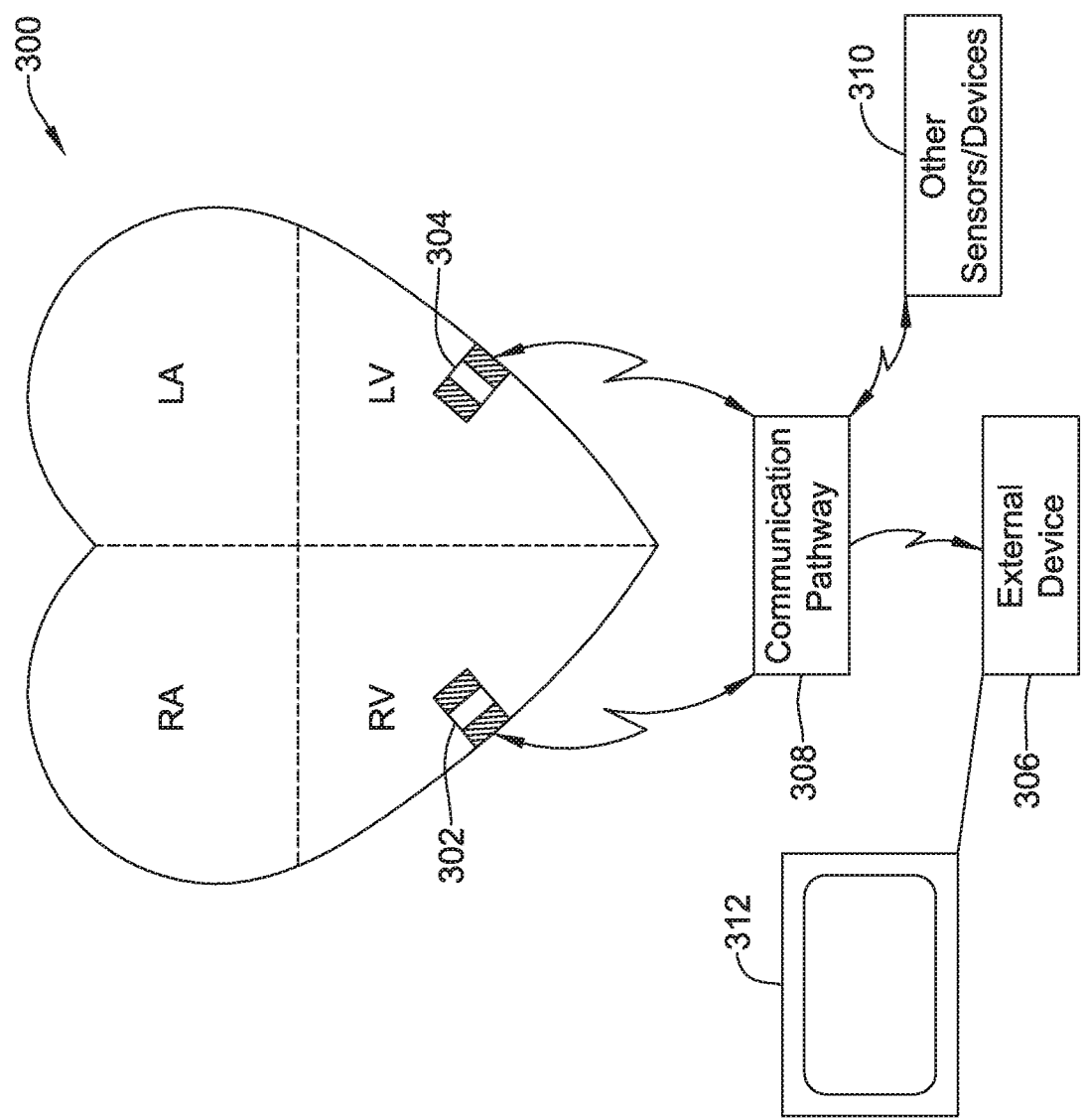
FIG. 3 is a schematic diagram of an exemplary medical system that includes multiple LCPs and/or other devices in communication with one another.

FIG. 3 shows an example medical device system with a communication pathway through which multiple medical devices 302, 304, 306, and/or 310 may communicate. In the example shown, the medical device system 300 may include LCPs 302 and 304, an external medical device 306, and other sensors/devices 310. The external device 306 may be any of the devices described previously with respect to MD 200. In some embodiments, the external device 306 may be provided with or be in communication with a display 312. The display 312 may be a personal computer, tablet computer, smart phone, laptop computer, or other display as desired. In some instances, the display 312 may include input means for receiving an input from a user. For example, the display 312 may also include a keyboard, mouse, actuatable (e.g., pushable) buttons, or a touchscreen display. These are just examples. The other sensors/devices 310 may be any of the devices described previously with respect to the MD 200. In some instances, the other sensors/devices 310 may include a sensor, such as an accelerometer or blood pressure sensor, or the like. In some cases, the other sensors/devices 310 may include an external programmer device that may be used to program one or more devices of the system 300.

Various devices of the system 300 may communicate via a communication pathway 308. For example, the LCPs 302 and/or 304 may sense intrinsic cardiac electrical signals and may communicate such signals to one or more other devices 302/304, 306, and 310 of the system 300 via the communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. In another example, the LCPs 302 and/or 304 may sense indications of blood pressure (e.g., via one or more pressure sensors) and indications of volume (e.g., via an impedance between the electrodes of an LCP or between LCPs via an ultrasound transducer placed within the LCP, or via strain sensors placed on the heart in communication with the LCP). In one example, one or more of the devices 302/304 may receive such signals and, based on the received signals, determine a pressure-volume loop, and in some cases may communicate such information to one or more other devices 302/304, 306, and 310 of the system 300 via the communication pathway 308.

It is contemplated that the communication pathway 308 may communicate using RF signals, inductive coupling, conductive coupling optical signals, acoustic signals, or any other signals suitable for communication. Additionally, in at least some examples, the device communication pathway 308 may comprise multiple signal types. For instance, the other sensors/device 310 may communicate with the external device 306 using a first signal type (e.g., RF communication) but communicate with the LCPs 302/304 using a second signal type (e.g., conducted communication, inductive communication). Further, in some examples, communication between devices may be limited. For instance, as described above, in some examples, the LCPs 302/304 may communicate with the external device 306 only through the other sensors/devices 310, where the LCPs 302/304 send signals to the other sensors/devices 310, and the other sensors/devices 310 relay the received signals to the external device 306.

In some cases, the communication pathway 308 may include conducted communication. Accordingly, devices of the system 300 may have components that allow for such conducted communication. For instance, the devices of the system 300 may be configured to transmit conducted communication signals (e.g., current and/or voltage pulses) into the patient's body via one or more electrodes of a transmitting device, and may receive the conducted communication signals (e.g., pulses) via one or more electrodes of a receiving device. The patient's body may "conduct" the conducted communication signals (e.g., pulses) from the one or more electrodes of the transmitting device to the electrodes of the receiving device in the system 300. In such examples, the delivered conducted communication signals (e.g., pulses) may differ from pacing or other therapy signals. For example, the devices of the system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

In some cases, the communication pathway 308 may include inductive communication, and when so provided, the devices of the system 300 may be configured to transmit/receive inductive communication signals.

Figure 4:
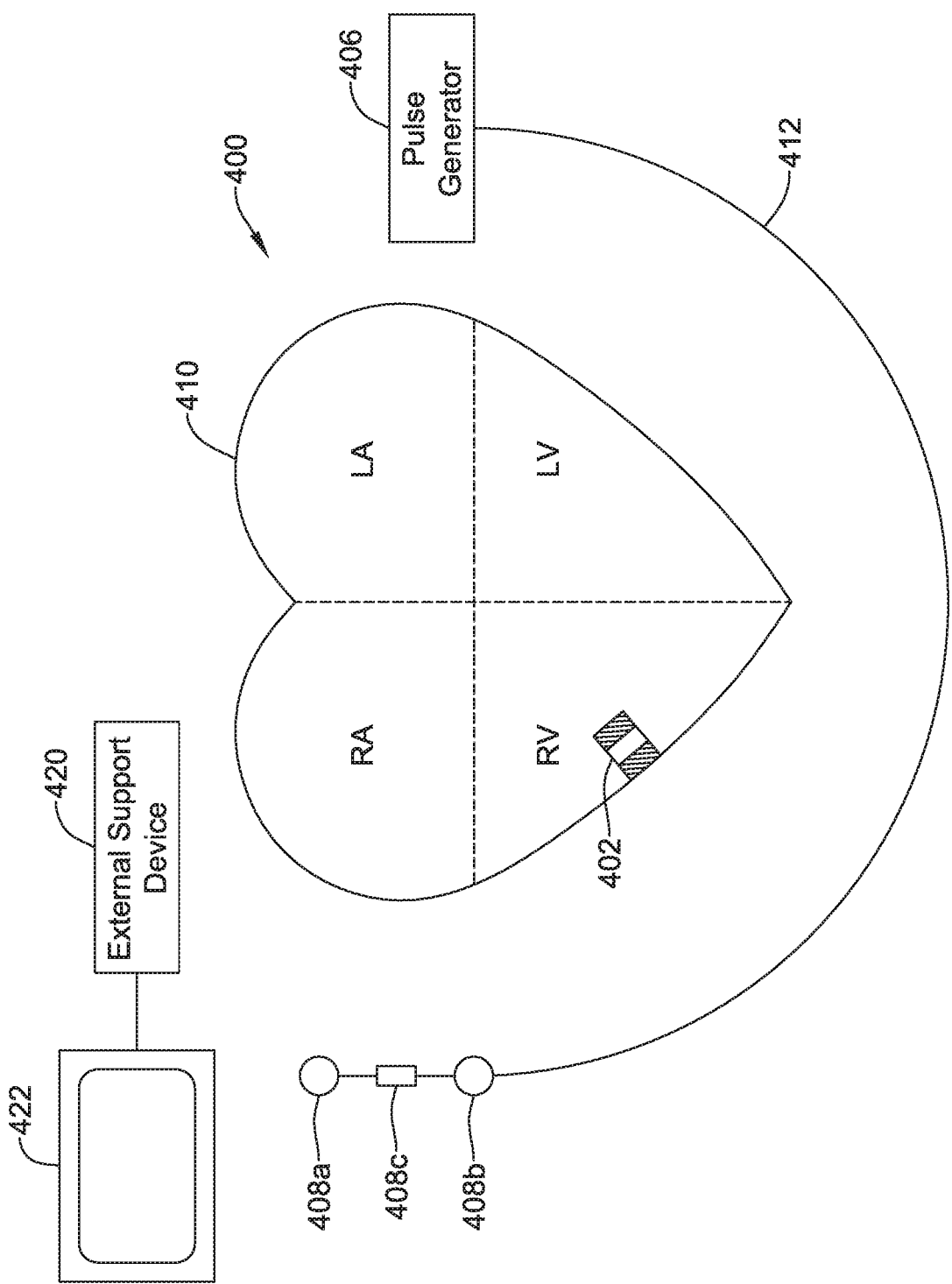
FIG. 4 is a schematic diagram of an exemplary medical system that includes an LCP and another medical device, in accordance with yet another example of the present disclosure.
Figure 5:
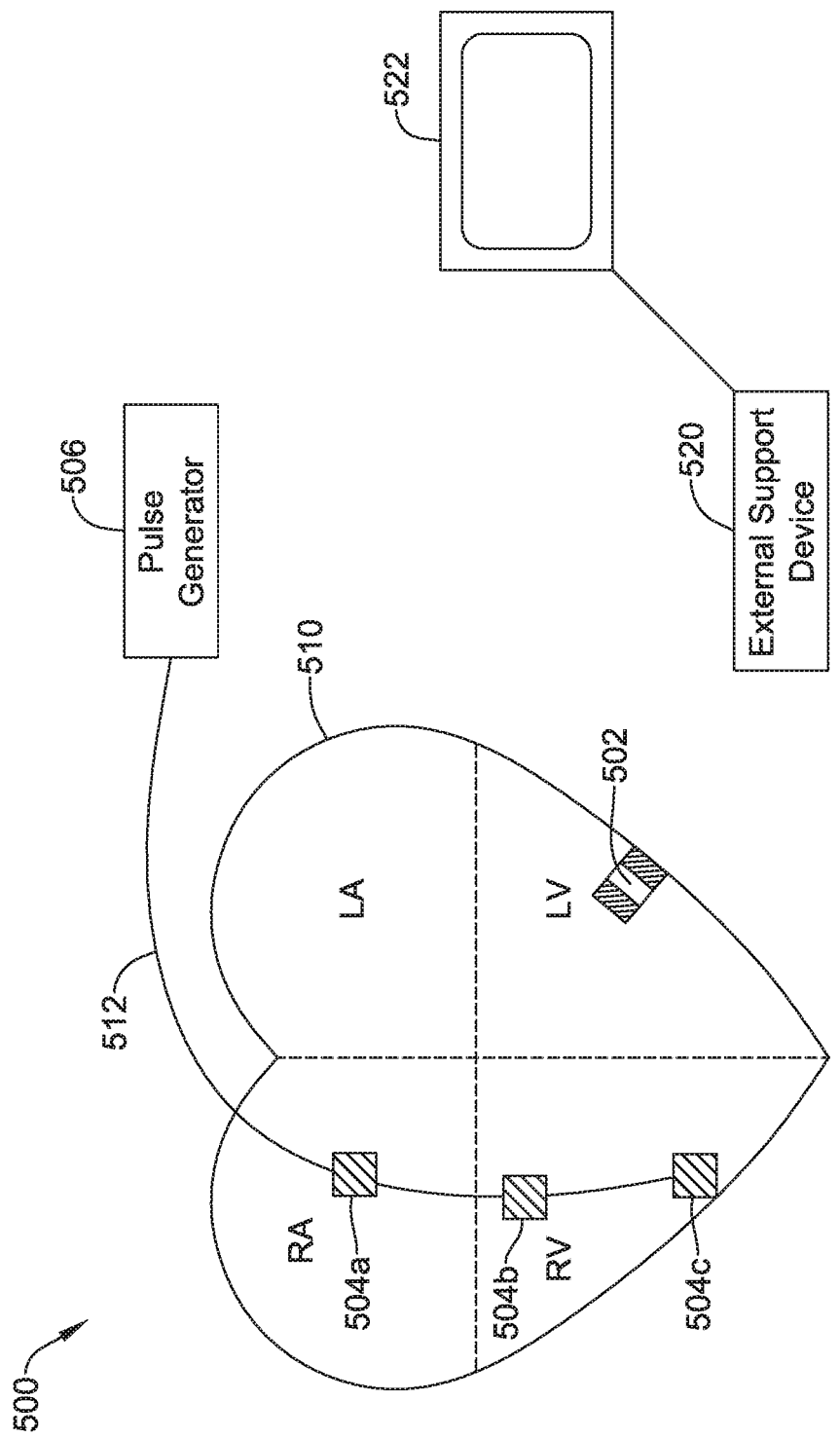
FIG. 5 is a schematic diagram of an exemplary medical system that includes an LCP and another medical device, in accordance with yet another example of the present disclosure.

FIGS. 4 and 5 show illustrative medical device systems that may be configured to operate according to techniques disclosed herein. In FIG. 4, an LCP 402 is shown fixed to the interior of the right ventricle of the heart 410, and a pulse generator 406 is shown coupled to a lead 412 having one or more electrodes 408a, 408b, 408c. In some cases, the pulse generator 406 may be part of a subcutaneous implantable cardioverter-defibrillator (S-ICD), and the one or more electrodes 408a, 408b, 408c may be positioned subcutaneously adjacent the heart. In some cases, the S-ICD lead may extend subcutaneously from the S-ICD can, around the sternum and one or more electrodes 408a, 408b, 408c may be positioned adjacent the interior surface of the sternum. In some cases, the LCP 402 may communicate with the subcutaneous implantable cardioverter-defibrillator (S-ICD).

In some cases, the LCP 402 may be in the left ventricle, right atrium or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 5, an LCP 502 is shown fixed to the interior of the left ventricle of the heart 510, and a pulse generator 506 is shown coupled to a lead 512 having one or more electrodes 504a, 504b, 504c. In some cases, the pulse generator 506 may be part of an implantable cardiac pacemaker (ICP) and/or an implantable cardioverter-defibrillator (ICD), and the one or more electrodes 504a, 504b, 504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. The external support devices 420 and 520 can be used to perform functions such as device identification, device programming and/or transfer of real-time and/or stored data between devices using one or more of the communication techniques described herein. As one example, communication between the external support device 420 and the pulse generator 406 is performed via a wireless mode, and communication between the pulse generator 406 and the LCP 402 is performed via a conducted mode. In some examples, communication between the LCP 402 and the external support device 420 is accomplished by sending communication information through the pulse generator 406. However, in other examples, communication between the LCP 402 and the external support device 420 may be via a communication module. In some embodiments, the external support devices 420, 520 may be provided with or be in communication with a display 422, 522. The display 422, 522 may be a personal computer, tablet computer, smart phone, laptop computer, or other display as desired. In some instances, the display 422, 522 may include input means for receiving an input from a user. For example, the display 422, 522 may also include a keyboard, mouse, actuatable buttons, or be a touchscreen display. These are just examples.

FIGS. 4-5 illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as the pulse generator 406 or 506, with at least one LCP capable of delivering defibrillation therapy. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

Figure 6:
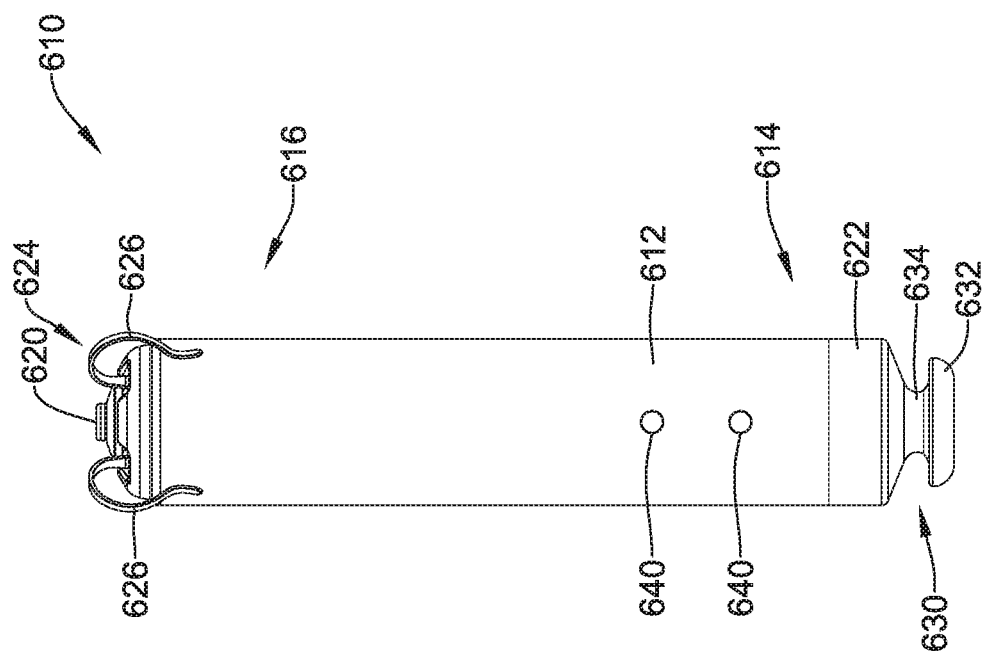
FIG. 6 is a side view of an illustrative LCP.

FIG. 6 is a side view of an illustrative implantable leadless cardiac pacemaker (LCP) 610. The LCP 610 may be similar in form and function to the LCP 100 described above. The LCP 610 may include any of the modules and/or structural features described herein. The LCP 610 may include a shell or housing 612 having a proximal end 614 and a distal end 616. The illustrative LCP 610 includes a first electrode 620 secured relative to the housing 612 and positioned adjacent to the distal end 616 of the housing 612 and a second electrode 622 secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. The electrodes 620, 622 may be sensing and/or pacing electrodes to provide electro-therapy and/or sensing capabilities. The first electrode 620 may be capable of being positioned against or may otherwise contact the cardiac tissue of the heart while the second electrode 622 may be spaced away from the first electrode 620. The first and/or second electrodes 620, 622 may be exposed to the environment outside the housing 612 (e.g., to blood and/or tissue).

It is contemplated that the housing 612 may take a variety of different shapes. For example, in some cases, the housing 612 may have a generally cylindrical shape. In other cases, the housing 612 may have a half-dome shape. In yet other embodiments, the housing 612 may be a rectangular prism. It is contemplated that the housing may take any cross sectional shape desired, including but not limited to annular, polygonal, oblong, square, etc.

In some cases, the LCP 610 may include a pulse generator (e.g., electrical circuitry) and a power source (e.g., a battery) within the housing 612 to provide electrical signals to the electrodes 620, 622 to control the pacing/sensing electrodes 620, 622. While not explicitly shown, the LCP 610 may also include a communications module, an electrical sensing module, a mechanical sensing module, and/or a processing module, and the associated circuitry, similar in form and function to the modules 102, 106, 108, 110 described above. The various modules and electrical circuitry may be disposed within the housing 612. Electrical communication between the pulse generator and the electrodes 620, 622 may provide electrical stimulation to heart tissue and/or sense a physiological condition.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. As shown in FIG. 6, in some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure (not explicitly shown) extending from or recessed within the head portion 632. The tether retention structure may define an opening configured to receive a tether or other anchoring mechanism therethrough. The retention structure may take any shape that provides an enclosed perimeter surrounding the opening such that a tether may be securably and releasably passed (e.g., looped) through the opening. In some cases, the retention structure may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

It is contemplated that the LCP 610 may include one or more pressure sensors 640 coupled to or formed within the housing 612 such that the pressure sensor(s) is exposed to and/or otherwise operationally coupled with the environment outside the housing 612 to measure blood pressures within the heart. In some cases, the one or more pressure sensors 640 may be coupled to an exterior surface of the housing 612. In other cases, the one or more pressures sensors 640 may be positioned within the housing 612 with a pressure acting on the housing and/or a port on the housing 612 to affect the pressure sensor 640. For example, if the LCP 610 is placed in the right ventricle, the pressure sensor(s) 640 may measure the pressure within the right ventricle. If the LCP 610 is placed in another portion of the heart (such as one of the atriums or the left ventricle), the pressures sensor(s) may measure the pressure within that portion of the heart. It is contemplated that the pressure sensor(s) 640 may be sensitive enough to detect a pressure change in the right atrium (e.g. atrial kick) when the LCP is placed in the right ventricle. Some illustrative pressure sensor configurations will be described in more detail herein.

In some instances, the pressure sensor(s) 640 may include a deformable diaphragm formed in part or in whole from a piezoelectric material which does not require external power to function. In some instances, the pressure sensor(s) 640 may include a MEMS device, such as a MEMS device with a pressure diaphragm with one or more piezoelectric sensors and/or piezoresistors on the diaphragm, a capacitor-Micromachined Ultrasonic Transducer (cMUT), a condenser, a micromanometer, a surface acoustic wave (SAW) device, and/or any other suitable sensor adapted for measuring a pressure exerted on the diaphragm. Some illustrative but non-limiting pressure sensors and configurations are describe in commonly assigned Patent Application No. 62/413,766 entitled "IMPLANTABLE MEDICAL DEVICE WITH PRESSURE SENSOR and filed on Oct. 27, 2016, which is hereby incorporated by reference. It is contemplated that when piezoresistors are used, a piezo-resistive bridge may be operated in a low power mode (e.g., limited duty-cycle excitation) to reduce the power demand of the sensor. In some cases, the gain may be modulated to further reduce power demands.

When a piezoelectric material is used, the piezoelectric material may generate an electrical voltage (and/or electric current) between a first pressure sensor electrode and a second pressure sensor electrode in response to a pressure change applied to the piezoelectric material. The electrical voltage (and/or electric current) may be representative of the pressure change. In this instance, the piezoelectric material may not require any external power, but rather the piezoelectric material itself may convert energy extracted from the change in pressure into an electrical voltage (and/or electric current), which can then be used by the LCP to identify a pressure change. In some cases, it may not be necessary or even desirable to measure an absolute pressure value. Instead, just detecting a pressure change is all that is necessary to identify certain pressure events.

The pressures sensor(s) 640 may be part of a mechanical sensing module described herein. It is contemplated that the pressure measurements obtained from the pressures sensor(s) 640 may be used to generate a pressure curve over cardiac cycles. The pressure sensor(s) 640 may measure/sense pressure in the chamber in which the LCP 610 is implanted. For example, an LCP 610 implanted in the right ventricle (RV) could sense RV pressure. It is further contemplated that the pressure sensor(s) 640 may be sensitive enough to detect pressure changes in other chambers as well as the chamber in which the LCP 610 is positioned. For example, when the LCP 610 is positioned within the right ventricle, the pressure sensor(s) 640 may detect pressure changes in the right atrium (e.g. atrial kick) in addition to pressure changes in the right ventricle.

In some cases, sensing atrial pressure events may allow the device 610 to detect an atrial contraction, resulting in for example an atrial kick. Such a change in atrial pressure event may be used by an LCP in the right ventricle to time a pacing pulse for the ventricle in support of treating bradycardia events. In some cases, the timing of the ventricle pacing pulse may be adjusted to maximize the amount of blood entering the right ventricle through passive filling. In some instances, this may include adjusting an AV delay relative to the atrial fiducial (e.g. atrial kick). In some cases, a measured pressure change over time may be used to support management of a CRT cardiac therapy (if placed in the left ventricle), patient health status monitoring and/or any other suitable goal. It is contemplated measuring pressure events in both the ventricle and atrium using a single LCP may replicate a dual chamber system with a single device. For example, such a system may enable a device to be positioned in the ventricle while listening to both the ventricle and the atrium and pacing accordingly (e.g., a VDD device).

The pressure sensor(s) 640 may be configured (either alone or in combination with other circuitry in the LCP 610) to derive a change in pressure over time and may be used to adjust atrium to ventricle (AV) pacing delay to optimize pacing for treating bradycardia events. In some cases, the pressure sensor(s) 640 may be configured to detect a-waves (e.g. atrial kick) and change the pacing timing of the LCP 610 for ventricular pacing in relation to the contraction of the right atrium. It is further contemplated that sensing pressure could be used during the implant procedure to optimize the placement of the LCP 610 in the chamber (e.g., RV by sampling at different implant locations and using the best location). In some cases, frequent pressure monitoring may be beneficial for management of heart failure patients. Frequent pressure monitoring may also be useful for patients with chronic heart disease, hypertension, regurgitation, valve issues, atrial contraction detection, and to aid in addressing other problems. It is further contemplated that the pressure sensor(s) 640 may be used for monitoring respiration and associated diseases (e.g., chronic obstructive pulmonary disease (COPD), etc.). These are just examples.

In some cases, pressure readings may be taken in combination with a cardiac chamber volume measurement such an impedance measurement (e.g., the impedance between electrodes 620 and 622) to generate a pressure-impedance loop for one or more cardiac cycles. The impedance may be a surrogate for chamber volume, and thus the pressure-impedance loop may be representative of a pressure-volume loop for the heart H.

Figure 7A:
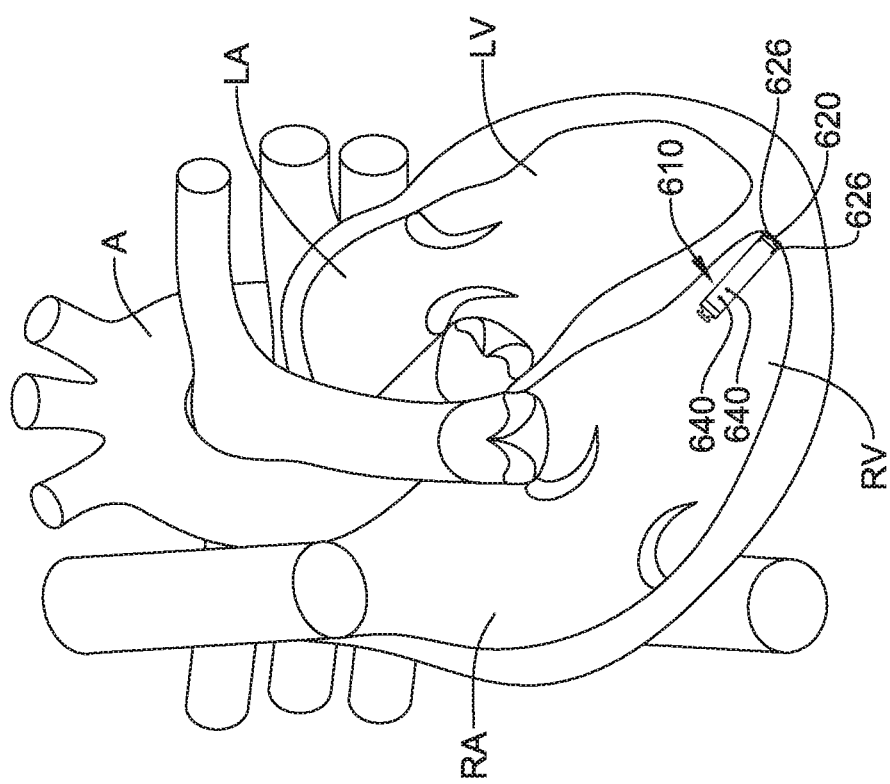
FIG. 7A is a plan view of an example LCP implanted within a heart during ventricular filling.
Figure 7B:
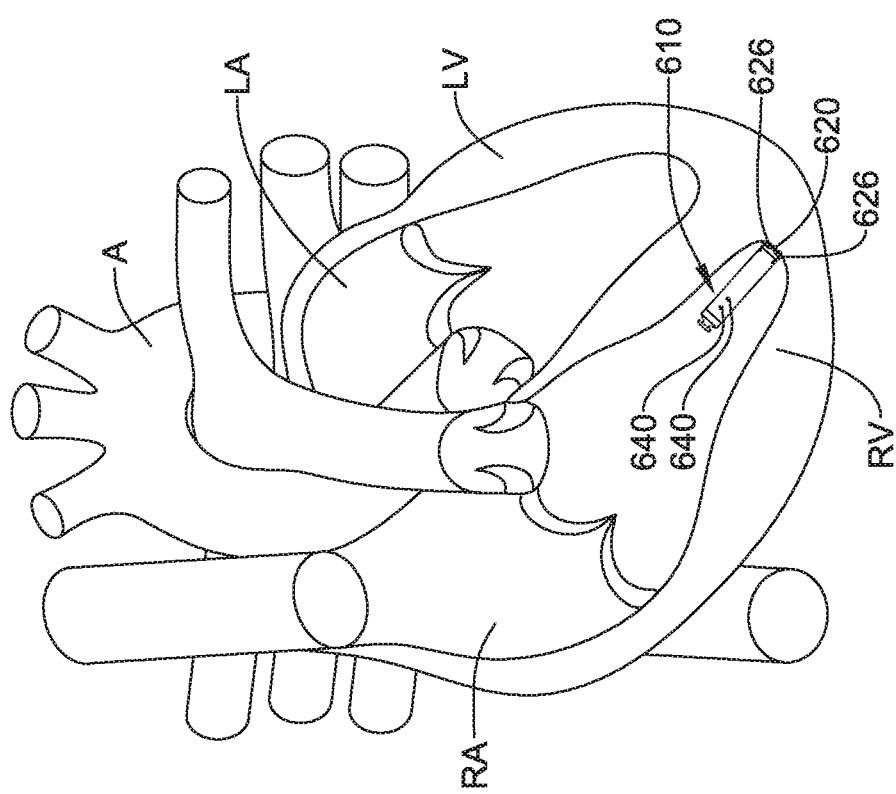
FIG. 7B is a plan view of an example LCP implanted within a heart during ventricular contraction.

FIG. 7A is a plan view of the example leadless cardiac pacing device 610 implanted within a right ventricle RV of the heart H during ventricular filling. The right atrium RA, left ventricle LV, left atrium LA, and aorta A are also illustrated. FIG. 7B is a plan view of the leadless cardiac pacing device 610 implanted within a right ventricle of the heart H during ventricular contraction. These figures illustrate how the volume of the right ventricle may change over a cardiac cycle. As can be seen in FIGS. 7A and 7B, the volume of the right ventricle during ventricular filling is larger than the volume of the right ventricle of the heart during ventricular contraction.

In some cases, the processing module and/or other control circuitry may capture, at a time point within each of one or more cardiac cycles, one or more pressures within the heart (e.g., right ventricle and/or right atrium), resulting in one or more pressure data points. These one or more data points may be used, in combination with other pressure data points taken at different times during the one or more cardiac cycles, to generate a pressure curve. In some cases, one or more parameters may be extracted or derived from the pressure curve. The pressure curve may be used to facilitate cardiac resynchronization therapy (CRT), patient health status monitoring, and/or the management of a non-CRT cardiac therapy.

Figure 8:
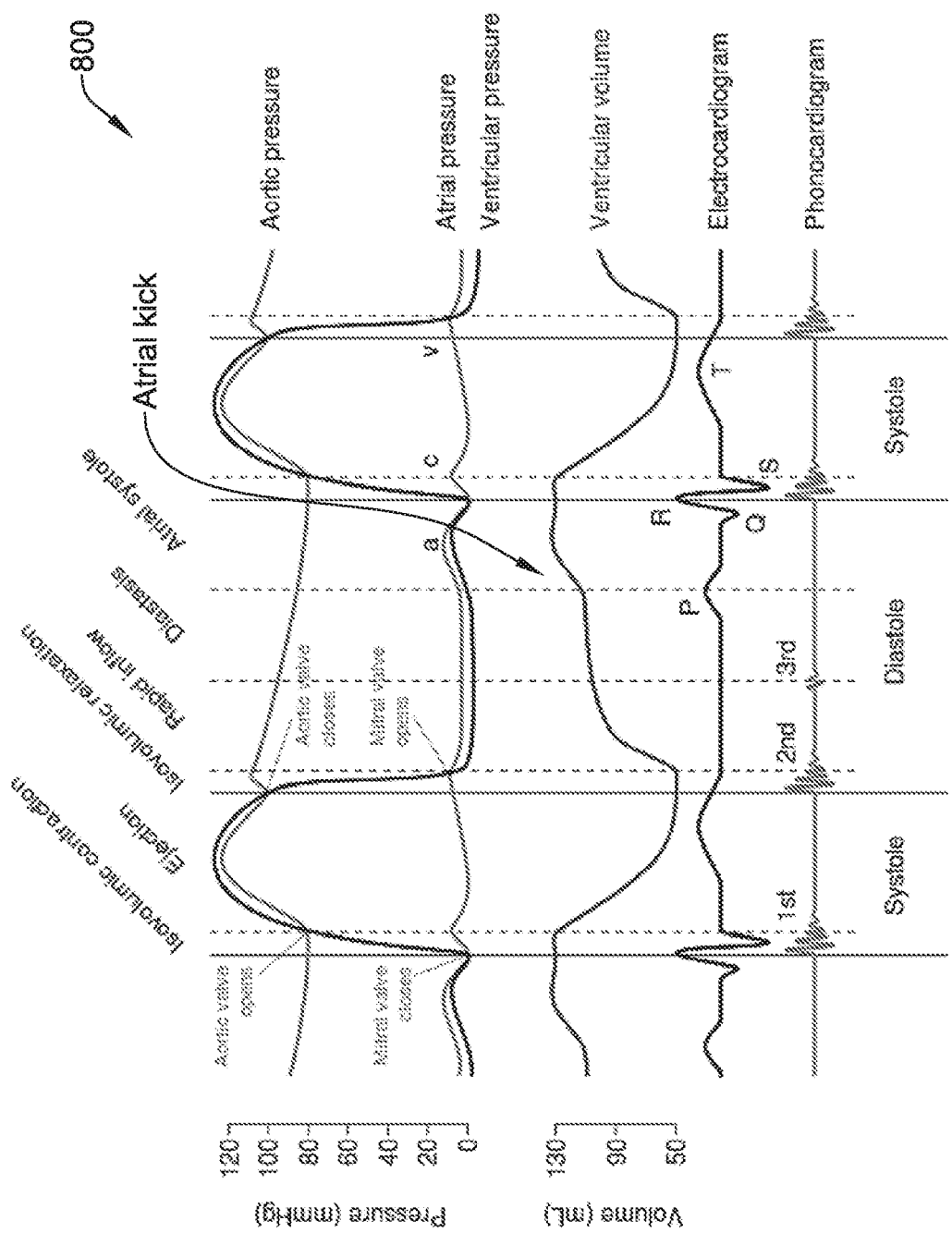
FIG. 8 is a graph showing example pressures and volumes within the heart over time.

FIG. 8 is a graph 800 showing example pressures and volumes within a heart over time. More specifically, FIG. 8 depicts the aortic pressure, left ventricular pressure, left atrial pressure, left ventricular volume, an electrocardiogram (ECG or egram), and heart sounds of the heart H. A cardiac cycle may begin with diastole, and the mitral valve opens. The ventricular pressure falls below the atrial pressure, resulting in the ventricular filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricular volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats. Contractions of the atria are initiated near the end of ventricular diastole. The active atrial contraction pushes or forces additional volumes of blood into the ventricles (often referred to as "atrial kick") in addition to the volumes associated with passive filling. In some cases, the atrial kick contributes in the range of about 20% of the volume of blood toward ventricular preload. At normal heart rates, the atrial contractions are considered essential for adequate ventricular filling. However, as heart rates increase, atrial filling becomes increasingly important for ventricular filling because the time interval between contractions for passive filling becomes progressively shorter. Cardiac pressure curves for the pulmonary artery, the right atrium, and the right ventricle, and the cardiac volume curve for the right ventricle, similar to those illustrated in FIG. 8 for the left part of the heart, may be likewise generated. Typically, the cardiac pressure in the right ventricle is lower than the cardiac pressure in the left ventricle.

In one example, the heart sound signals can be recorded using acoustic sensors, (for example, a microphone), which capture the acoustic waves resulted from heart sounds. In another example, the heart sound signals can be recorded using accelerometers or pressure sensors that capture the accelerations or pressure waves caused by heart sounds. The heart sound signals can be recorded within or outside the heart. These are just examples.

Figure 9:
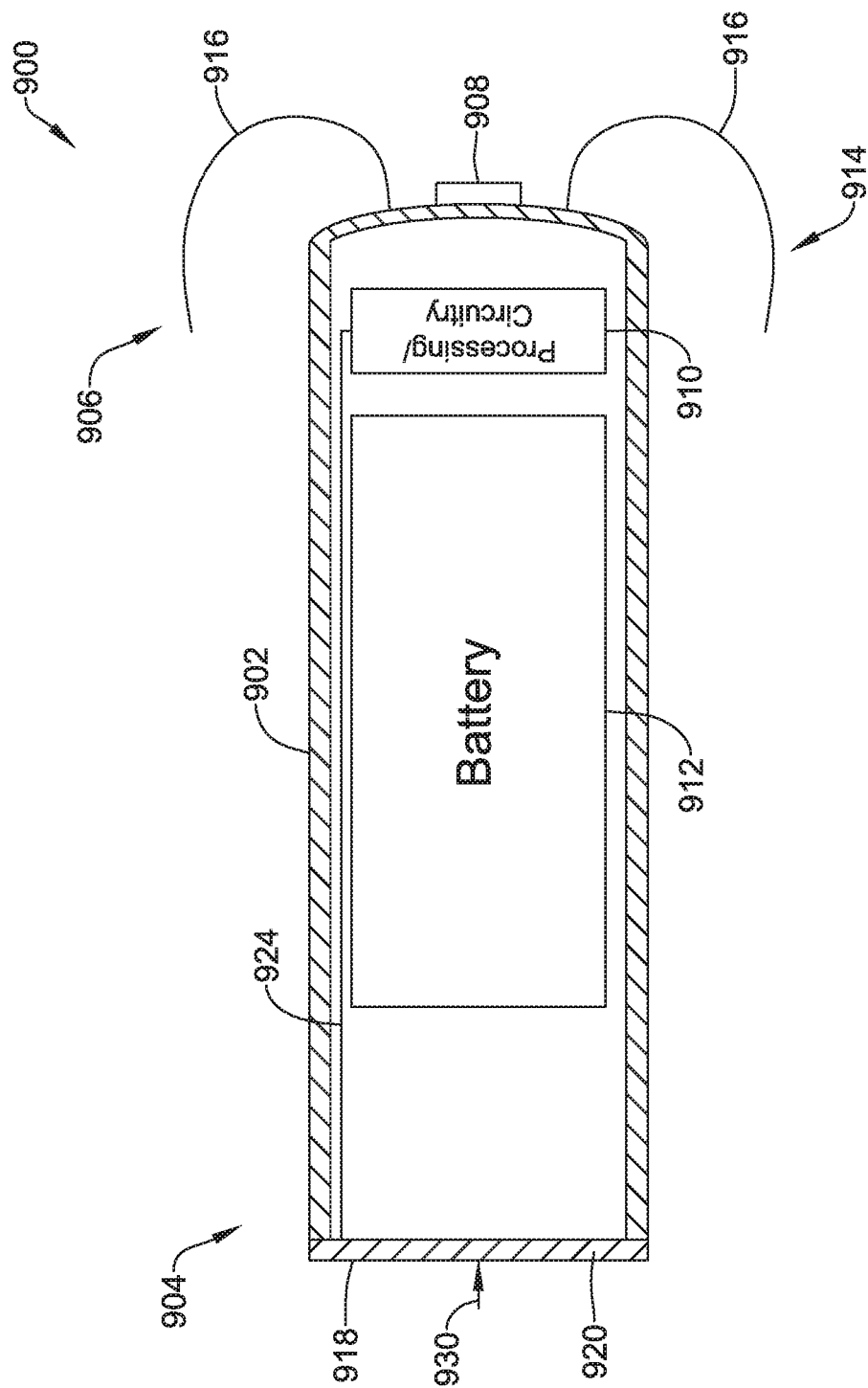
FIG. 9 is a schematic cross-sectional view of an illustrative LCP.

FIG. 9 is a cross-section of an illustrative implantable leadless cardiac pacemaker (LCP) 900. The LCP 900 may be similar in form and function to the LCPs 100, 610 described above. The LCP 900 may include any of the modules and/or structural features described above with respect to the LCPs 100, 610. The LCP 900 may include a shell or housing 902 having a proximal end 904 and a distal end 906. In the example shown, the LCP 900 does not include a docking member. However, in some cases, a docking member may be provided, such as a cage, a head or other feature extending proximally from adjacent the side walls of the housing 902. The illustrative LCP 900 includes a first electrode 908 secured relative to the housing 902 and positioned adjacent to the distal end 906 of the housing 902, and a second electrode (not explicitly shown) secured relative to the housing 902 and positioned adjacent to the proximal end 904 of the housing 902. In some instances, the first electrode 908 may be positioned on a distal end surface facing distally. In some cases, the housing 902 may include a conductive material and may be insulated along a portion of its length. A section along the proximal end 904 may be free of insulation so as to define the second electrode. The electrodes 908 may be sensing and/or pacing electrodes to aid in providing electro-therapy and/or sensing capabilities. The first electrode 908 may be capable of being positioned against or may otherwise contact the cardiac tissue of the heart while the second electrode may be spaced away from the first electrode 908. The first and/or second electrodes 908 may be exposed to the environment outside the housing 902 (e.g., to blood and/or tissue).

In some cases, the LCP 900 may include a pulse generator (e.g., electrical circuitry) 910 and a power source (e.g., a battery) 912 within the housing 902 to provide and/or receive electrical signals via the first and second electrodes. While not explicitly shown in FIG. 9, the LCP 900 may also include a communications module, an electrical sensing module, a mechanical sensing module, and/or a processing module, and associated circuitry, similar in form and function to the modules 102, 106, 108, 110 described above. The various modules and electrical circuitry may be disposed within the housing 902. Electrical communication between the pulse generator and the electrodes may provide electrical stimulation to heart tissue and/or sense a physiological condition.

In the example shown, the LCP 900 further includes a fixation mechanism 914 proximate the distal end 906 of the housing 902. The fixation mechanism 914 is configured to attach the LCP 900 to a wall of the heart H, or otherwise anchor the LCP 900 to the anatomy of the patient. As shown in FIG. 9, in some instances, the fixation mechanism 914 may include one or more, or a plurality of hooks or tines 916 anchored into the cardiac tissue of the heart H to attach the LCP 900 to a tissue wall. In other instances, the fixation mechanism 914 may include one or more, or a plurality of passive tines, configured to entangle with trabeculae within the chamber of the heart H and/or a helical fixation anchor configured to be screwed into a tissue wall to anchor the LCP 900 to the heart H. These are just examples.

The housing 902 may include a proximal end surface 918 facing proximally (e.g., in a generally opposite direction from the distal end surface. In some instances, the proximal end surface 918 of the housing 902 may form a diaphragm 920. In some cases, the diaphragm 920 may be formed from the housing material itself. When so provided, the wall thickness of the housing in the region of the diaphragm 920 may be thinned to increase the flexibility of the diaphragm 920 to as to be responsive (e.g. sufficiently deformable) to a pressure range of interest. In other cases, the diaphragm 920 may be formed from another material, such as but not limited to titanium, titanium foil, silicone, polyimides, etc. to form a deformable or movable diaphragm 920 that is responsive to a pressure of interest applied to the diaphragm 920. In some instances, the diaphragm 920 may be titanium or titanium foil on polyvinylidene fluoride (PVDF). In some instances, the diaphragm 920 may be formed from a piezoelectric material and/or may include a piezoelectric layer.

A piezoelectric material may exhibit the piezoelectric effect, or the ability to generate a voltage (and/or current) when the material is subjected to a mechanical stress or vibration. Some illustrative piezoelectric materials may include, but are not limited to some naturally occurring crystals (e.g., quartz, sucrose, Rochelle salt, topaz, lead titanate, etc.), synthetic crystals, ceramics (e.g., barium titanate, lead zirconate titanate (PZT), zinc oxide, etc.), polymers (e.g., polyvinylidene fluoride (PVDF)), etc. This list is not intended to be exhaustive of all types of piezoelectric materials, but rather illustrative of some example materials. When used as part of the hermetic seal around the LCP, it is contemplated that the material (piezoelectric or otherwise) selected for the diaphragm 920 may be hermetic. For example, the material should be capable of preventing blood from diffusing through the diaphragm and into the interior or the LCP.

In any event, the diaphragm 920 may be fabricated to flex or deform as the pressure (external to the housing 902) in the heart (e.g., right ventricle and/or right atrium) changes, as will be described in more detail herein. While the entire proximal end surface 918 may form the diaphragm 920, it is contemplated that only a portion of the end surface 918 may form the diaphragm 920. In some cases, the diaphragm 920 may be 1 millimeter in diameter or less. In other cases, the diaphragm 920 may be greater than 1 millimeter in diameter. In some cases, the diaphragm 920 may have a round shape. In other cases, the diaphragm 920 may have a square, rectangular or any other suitable shape. In some cases, the diaphragm 920 may not have a uniform thickness. In some cases, the diaphragm 920 may have thicker bossed regions that provide support to, for example, increase the linearity of the deformation of the diaphragm 920 with pressure.

In some cases, the diaphragm 920 may be formed from a piezoelectric material. As the diaphragm flexes or deforms in response to an external pressure, a voltage (and/or current) may be generated by the piezoelectric material between sensor electrodes on opposing sides of the piezoelectric material. The generated voltage (and/or current) may be transferred via one or more electrical conductors 924 to the electrical circuitry 910, which may identify a pressure event and/or pressure value. In some cases, the generated voltage (and/or current) may reflect a change in pressure over time as opposed to an absolute or gauge pressure. When so provided, a reference pressure may not be required. In any event, the change in pressure over time may be sufficient to identify events such as the atrial contraction (e.g., atrial kick), ventricular filling, ventricular ejection, etc. In some instances, the electrical circuitry 910 may be configured to obtain pressure measurements at a sample rate of greater than 100 Hertz (Hz), but this is not required. This may allow for pressure measurements to be used to determine characteristics of the cardiac cycle including, but not limited to, dP/dT, dicrotic notch, etc.

In some cases, the one or more electrical conductors 924 may include a first electrical conductor coupled to a first electrode on a first side of the piezoelectric material, and a second electrical conductor coupled a second electrode on a second opposite side of the piezoelectric material, such that the voltage (and/or current) generated is transmitted to the electrical circuitry 910.

The diaphragm 920 need not be placed on the proximal end surface 918 of the housing 902 such as shown in FIG. 9. It is contemplated that the diaphragm 920 may be formed in any surface that is exposed to the environment outside of the housing 902. In some cases, locating the diaphragm 920 on or adjacent to the proximal end 904 of the housing 902 may orientate the diaphragm towards the heart valves (when the LCP 900 is positioned in the apex of the heart) and in-line with expected maximum pressure changes within the heart, which may achieve higher signal-to-noise (SN) levels. This may also locate the diaphragm 920 away from the heart wall, which may reduce the likelihood that the diaphragm 920 will become fibrossed-over. In some cases, the diaphragm 920 may be coated with an anti-thrombogenic coating to help prevent tissue growth on or over the diaphragm 920.

In the example of FIG. 9, a battery 912 is shown adjacent the diaphragm 920. However, many different configurations of the internal components of the LCP 900 are contemplated. In the example shown, the processing module (e.g., circuitry or control electronics) 910 is positioned in a distal portion 906 of the housing 902 adjacent to the distal electrode. The one or more electrical conductors 924 may be formed of a polyimide or similar interconnect having a cross-sectional dimension in the range of less than 250 microns. It is contemplated that the inside surface of the housing 902 may be electrically insulated and the electrical conductors 924 (e.g., trace) may be positioned on the inside surface of the housing 902 or along the outer surface of the battery 912, as desired. Alternatively, wires or a ribbon cable may be used. These are just examples.

In some cases, the electrical circuitry 910 may be configured to obtain pressure measurements at predetermined intervals over one or more cardiac cycles. In other instances, the electrical circuitry 910 may be configured to obtain a pressure measurement in response to a specific cardiac event or at a specific time in a cardiac cycle. For example, the circuitry 910 may be configured to use one or more cardiac signals sensed by the first electrode 908 and/or second electrode to determine when the patient's heart is in a first phase of a cardiac cycle. The circuitry 910 may be configured to determine a pressure exterior to the housing 902 based at least in part on the pressure obtained during the first phase of the cardiac cycle. In some cases, the first phase may be systole and in other cases the first phase may be diastole. The circuitry 910 may also be configured to determine a pressure exterior to the housing 902 based at least in part on the pressure taken during a second phase of the cardiac cycle. It is contemplated that the circuitry 910 may be further configured to detect heart sounds of the patient's heart based at least in part on the pressure sensor output signal. For example, the first heart sound may be a timing fiducial for a sudden increase in pressure while the second heart sound may be a timing fiducial for a sudden decrease in pressure.

In some cases, the circuitry 910 of the LCP 900 may be configured to obtain a plurality of pressure readings over one or more cardiac cycles. The pressure readings may be plotted (either by the circuitry 910 or an external device) to form a graph similar to the one shown in FIG. 8. Various parameters related to the function of the heart can be extrapolated from the graph including but not limited to peak to peak measurements, dP/dT, time averaged values, inotropic response of the ventricle, etc. In some instances, the pressure measurements may be compared to calibration values (e.g., measurements taken at the time of implantation of the LCP 900). It is further contemplated that the diaphragm 920 may be sensitive enough to generate a voltage in response to a pressure increase in a chamber different from the chamber in which the LCP 900 is implanted. For example, when the LCP 900 is implanted in the right ventricle, the diaphragm may generate a voltage in response to a pressure increase in the right atrium (e.g. atrial kick) as well as a pressure increase in the right ventricle.

In some cases, the diaphragm 920 may be formed of the same material and of the same thickness as the remaining portion of the housing 902. For example, the housing 902 may flex or deform to transfer a pressure external to the housing 902 to a layer of piezoelectric material located within the housing 612. For example, the housing 902 may have a compliance such that the relative movement of the housing 902 in response to the external pressure may be operatively coupled to a piezoelectric material. The resulting voltage (and/or current) generated by the piezoelectric material may be calibrated relative to external pressures prior to implantation of the LCP 900 in a patient. The calibration data may be stored in the memory and/or electrical circuitry of the LCP 900. In some cases, there may be some pressure loss (e.g., in the range of 1-20% or more) between the pressure exerted on the housing 902 and the pressure applied to the piezoelectric material, depending on the placement of the piezoelectric material. This pressure loss may be compensated for (e.g., nullified) by adjusting the algorithm that converts the voltage (and/or current) generated by the piezoelectric material to a pressure using the calibration data stored in the LCP 900.

Figure 10:
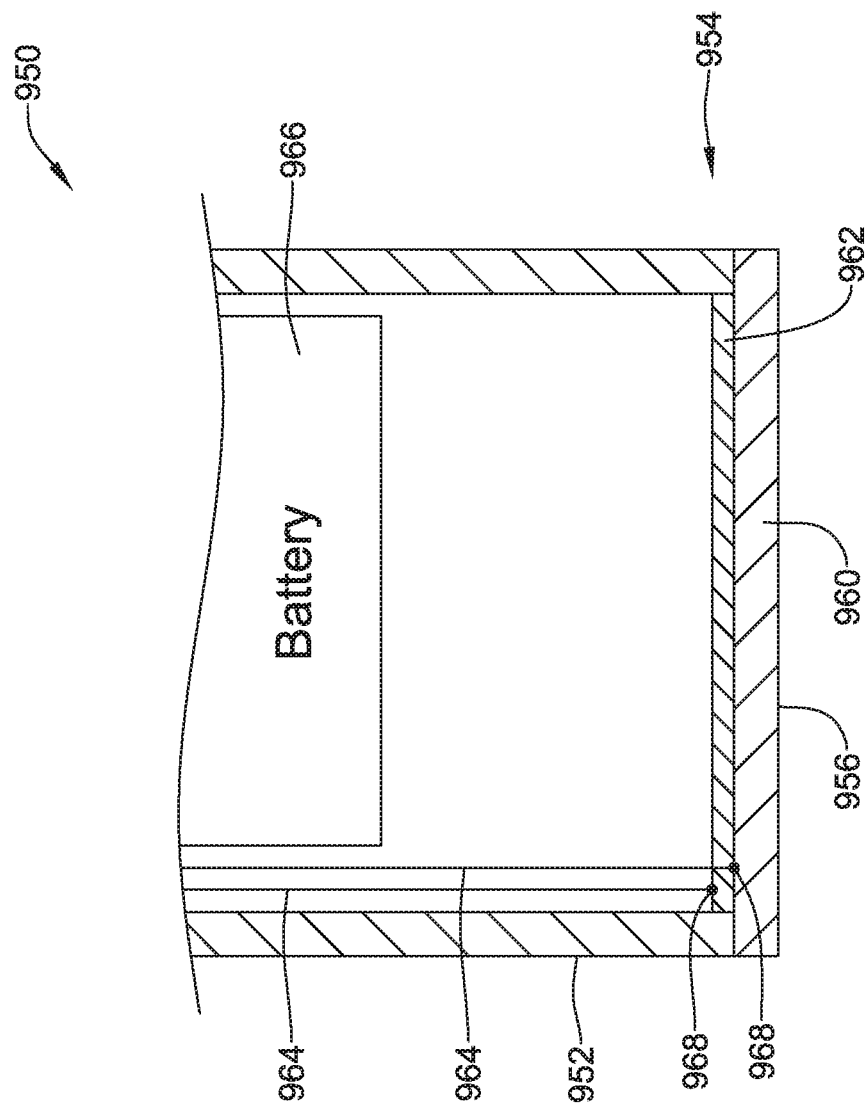
FIG. 10 is a schematic cross-sectional view of an illustrative pressure sensor for use with an implantable medical device (IMD) such as an LCP.

FIG. 10 illustrates a proximal end portion 954 of another illustrative LCP 950 having a diaphragm 960 and a piezoelectric membrane 962. The LCP 950 may be similar in form and function to the LCPs 100, 610, 900 described above. The LCP 950 may include any of the modules and/or structural features described above with respect to the LCPs 100, 610, 900.

The illustrative LCP 950 may include a shell or housing 952 having a proximal end portion 954 and a distal end (not explicitly shown). The housing 952 may include a proximal end surface 956 facing proximally (e.g., in a generally opposite direction from the distal end surface). In some instances, the proximal end surface 956 of the housing 952 may form a diaphragm 960. In some cases, the diaphragm 960 may be formed from the housing material itself, but this is not required. When so provided, the wall thickness of the housing in the region of the diaphragm 960 may be thinned to increase the flexibility of the diaphragm 960, although this is not required. In some cases, the diaphragm 960 may be formed from another material, such as but not limited to titanium, titanium foil, silicone, polyimides, etc. to form a deformable or movable diaphragm 960 that is responsive to a desired pressure range applied to the diaphragm 960.

In the example shown, the diaphragm 960 may flex or deform and transfer a pressure applied from external to the housing 952 to a layer of piezoelectric material 962 located within the housing 952. For example, the housing 952 may have a compliance such that the relative movement of the housing 952 and/or diaphragm 960 in response to the external pressure may deform or otherwise apply a corresponding stress to a piezoelectric material or membrane 962. In some embodiments, the piezoelectric membrane 962 may be coupled to or positioned on an interior surface of the diaphragm 960, although this is not required.

As the diaphragm 960 flexes in response an external pressure, the piezoelectric membrane 962 may also flex. The applied stress to the piezoelectric membrane 962 may generate a voltage (and/or a current) between a first sensor electrode on one side of the piezoelectric membrane 962 and a second sensor electrode on the opposing side of the piezoelectric membrane 962. The voltage (and/or current) may be transferred via one or more electrical conductors 964 to the electrical circuitry of the LCP 950 where it may be converted from a voltage (and/or current) to a pressure reading. In some cases, the one or more electrical conductors 964 may include a first electrical conductor coupled to a first side of the piezoelectric membrane 962 and a second electrical conductor coupled a second side, opposite of the first side such that the voltage (and/or current) generated is transmitted to the electrical circuitry. In some instances, the electrical conductors may be coupled to the first and second sensor electrodes generally shown at 968.

The voltage (and/or current) generated by the piezoelectric material may be calibrated relative to external pressures applied prior to implantation of the LCP 950 in a patient. The calibration data may be stored in the memory and/or electrical circuitry of the LCP 950. In some cases, there may be some pressure loss (e.g., in the range of 1-20% or more) between the pressure exerted on the housing 952 and the pressure applied to the piezoelectric membrane 962. This pressure loss may be compensated for (e.g., nullified) by adjusting the algorithm that converts the voltage (and/or current) generated by the piezoelectric membrane 962 to a pressure using the calibration data stored in the LCP 950.

In the example of FIG. 10, the battery 966 is shown adjacent the diaphragm 960. However, many different configurations of the internal components of the LCP 950 are contemplated. In the example shown, the processing module (e.g., circuitry or control electronics) may be positioned in a distal portion of the housing 952 adjacent to the distal electrode. The one or more electrical conductors 964 may be formed of a polyimide or similar interconnect having a cross-sectional dimension in the range of less than 250 microns. It is contemplated that the inside surface of the housing 952 may be electrically insulated and the electrical conductors 964 (e.g., trace) may be positioned on the inside surface of the housing 952 or along the outer surface of the battery 966, as desired. Alternatively, wires or a ribbon cable may be used. These are just examples.

Figure 11:
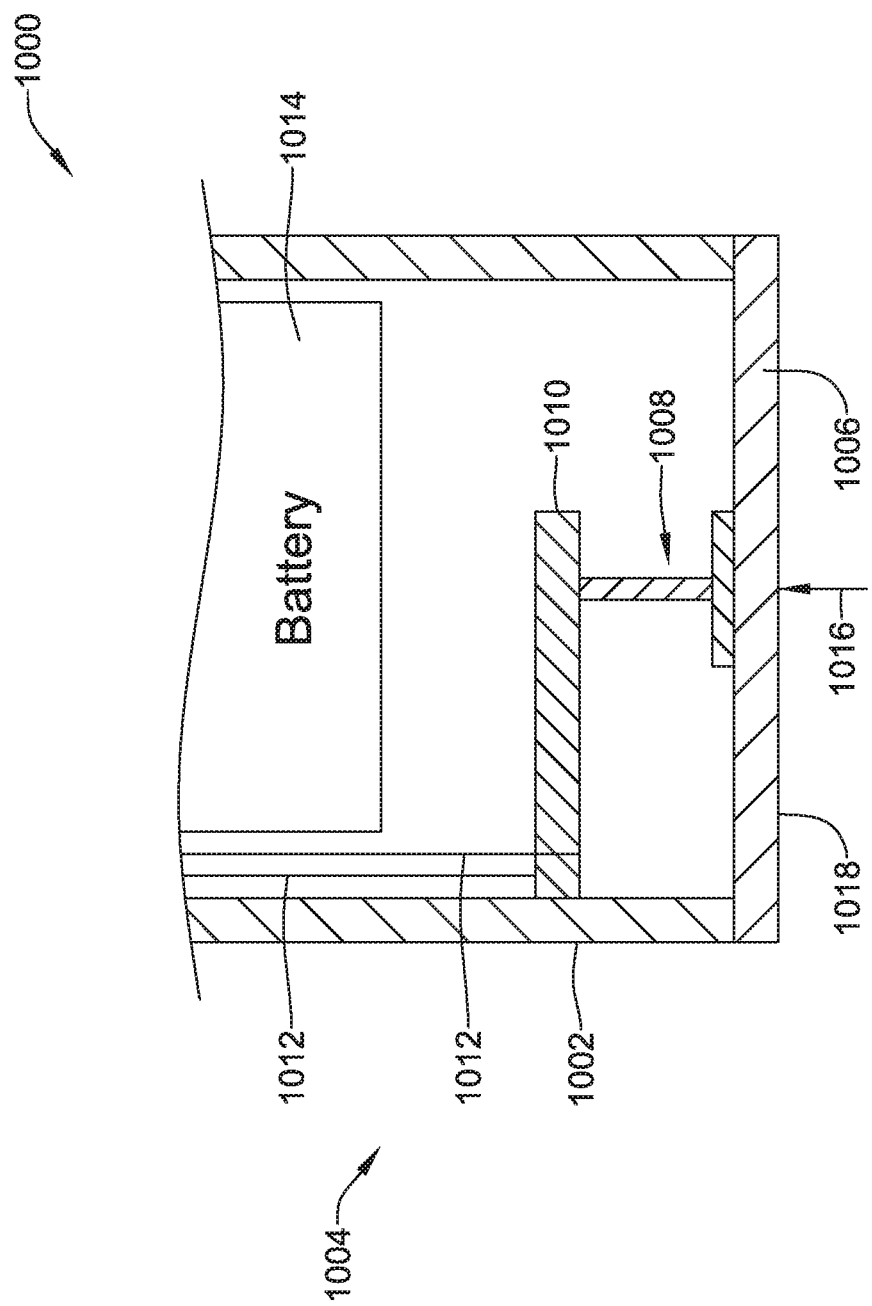
FIG. 11 is a schematic cross-sectional view of an illustrative pressure sensor for use with an 1 MB such as an LCP.

FIG. 11 illustrates a proximal end portion 1004 of another illustrative LCP 1000 having a diaphragm 1006 and a piezoelectric membrane 1010. The LCP 1000 may be similar in form and function to the LCPs 100, 610, 900 described above. The LCP 1000 may include any of the modules and/or structural features described above with respect to the LCPs 100, 610, 900.

The illustrative LCP 1000 may include a shell or housing 1002 having a proximal end portion 1004 and a distal end (not explicitly shown). The housing 1002 may include a proximal end surface 1018 facing proximally (e.g., in a generally opposite direction from the distal end surface). In some instances, the proximal end surface 1018 of the housing 1002 may form a diaphragm 1006. In some cases, the diaphragm 1006 may be formed from the housing material itself, although this is not required. When so provided, the wall thickness of the housing in the region of the diaphragm 1006 may be thinned to increase the flexibility of the diaphragm 1006, although this is not required. In some cases, the diaphragm 1006 may be formed from another material, such as but not limited to titanium, titanium foil, silicone, polyimides, etc. to form a deformable or movable diaphragm 1006 that is responsive to a desired pressure range applied to the diaphragm 1006.

The diaphragm 1006 may flex or deform to transfer a pressure external to the housing 1002 to a layer of piezoelectric material or a piezoelectric membrane 1010 located within the housing 1002. For example, the housing 1002 may have a compliance such that the relative movement of the housing 1002 and/or diaphragm 1006 in response to the external pressure may be mechanically coupled to a piezoelectric material or membrane 1010. In some embodiments, the piezoelectric membrane 1010 may be coupled to the diaphragm 1006 via a mechanical linkage or arm 1008. This may allow the piezoelectric membrane 1010 to be spaced a distance from the housing 1002 while still flexing in response to an externally applied pressure 1016. In some cases, it may be desirable for a more rigid piezoelectric material to be used, and the mechanical leverage provide by the mechanical linkage or arm 1008 may allow a more modest external pressure applied to the diaphragm 1006 to suitable stress the piezoelectric membrane 1010 to produce a desired voltage (and/or current). In the example shown, as the diaphragm 1006 flexes in response the external pressure 1016, the linkage 1008 also moves and transfers the force to the piezoelectric membrane 1010. The force applied to the piezoelectric membrane 1010 generates an voltage (and/or a current), which may be transferred via one or more electrical conductors 1012 to the electrical circuitry of the LCP 1000 where it is converted from an voltage (and/or current) to a pressure reading. In some cases, the one or more electrical conductors 1012 may include a first electrical conductor coupled to a first side of the piezoelectric membrane 1010 and a second electrical conductor coupled a second side, opposite of the first side of the piezoelectric membrane 1010, such that the voltage (and/or current) generated across the piezoelectric membrane 1010 is transmitted to the electrical circuitry. In some instances, the electrical conductors may be coupled to first and second pressure sensor electrodes positioned on opposite sides of the piezoelectric membrane 1010.

The voltage generated by the piezoelectric membrane 1010 may be calibrated relative to external pressures prior to implantation of the LCP 1000 in a patient. The calibration data may be stored in the memory and/or electrical circuitry of the LCP 1000. In some cases, there may be some pressure loss (e.g., in the range of 1-20% or more) between the pressure exerted on the housing 1002 and the pressure applied to the piezoelectric membrane 1010, depending on the linkage or arm 1008. This pressure loss may be compensated for (e.g., nullified) by adjusting the algorithm that converts the voltage (and/or current) generated by the piezoelectric material to a pressure using the calibration data stored in the LCP 1000.

In the example shown in FIG. 11, the battery 1014 is shown adjacent the piezoelectric membrane 1010. However, many different configurations of the internal components of the LCP 1000 are contemplated. In the example shown, the processing module (e.g., circuitry or control electronics) may be positioned in a distal portion of the housing 1002 adjacent to the distal electrode. The one or more electrical conductors 1012 may be formed of a polyimide or similar interconnect having a cross-sectional dimension in the range of less than 250 microns. It is contemplated that the inside surface of the housing 1002 may be electrically insulated and the electrical conductors 1012 (e.g., trace) may be positioned on the inside surface of the housing 1002 or along the outer surface of the battery 1014, as desired. Alternatively, wires or a ribbon cable may be used. These are just examples.

Figure 12:
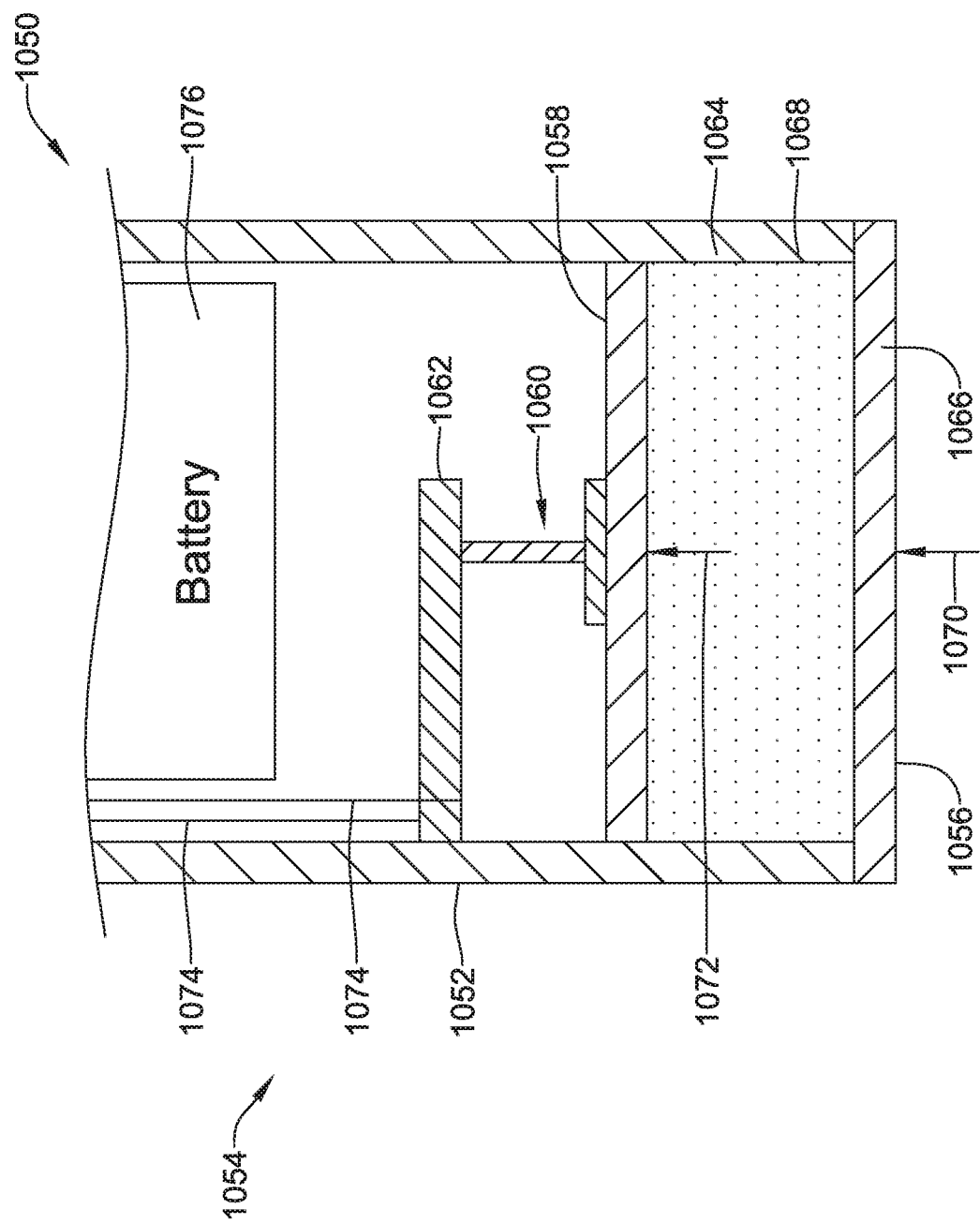
FIG. 12 is a schematic cross-sectional view of a proximal end portion of another illustrative LCP.

FIG. 12 illustrates a proximal end portion 1054 of another illustrative LCP 1050 having a diaphragm 1056 and a piezoelectric membrane 1062. The illustrative LCP 1050 may be similar in form and function to the LCPs 100, 610, 900 described above. The LCP 1050 may include any of the modules and/or structural features described above with respect to the LCPs 100, 610, 900.

The illustrative LCP 1050 may include a shell or housing 1052 having a proximal end portion 1054 and a distal end (not explicitly shown). The housing 1052 may include a proximal end surface 1066 facing proximally (e.g., in a generally opposite direction from the distal end surface). In some instances, the proximal end surface 1066 of the housing 1052 may form a diaphragm 1056. In some cases, the diaphragm 1056 may be formed from the housing material itself, but this is not required. When so provided, the wall thickness of the housing in the region of the diaphragm 1056 may be thinned to increase the flexibility of the diaphragm 1056, although this is not required. In other cases, the diaphragm 1056 may be formed from another material, such as but not limited to titanium, titanium foil, silicone, polyimides, etc. to form a deformable or movable diaphragm 1056 that is responsive to a desired pressure range applied to the diaphragm 1056.

The diaphragm 1056 may flex or deform to transfer a pressure external to the housing 1052 to a layer of piezoelectric material or a piezoelectric membrane 1062 located within the housing 1052. In the example shown, a cavity 1064 filled with a fluid 1068 may be positioned between the external diaphragm 1056 and an internal diaphragm 1058. The fluid filled cavity 1064 may be in fluid communication with the diaphragm(s) 1056, 1058 such that the fluid filled cavity 1064 may communicate a measure related to the pressure 1070 applied by the environment to the diaphragm 1056 of the housing 1052 ultimately to piezoelectric membrane 1062. The fluid filled cavity 1064 may be filled with an incompressible fluid 1068. In some cases, the fluid filled cavity 1064 may be filled with a non-conductive fluid 1068. In some cases, the fluid 1068 may be highly soluble to gases that may arise inside of the housing, particularly at body temperature (e.g., 37° C.). For example, the fluid 1068 may be highly soluble to hydrogen, helium, nitrogen, argon, water, and/or other gases or liquids that might arise inside of the housing as a result of, for example, outgassing of internal components of the LCP 1050.

The diaphragms 1056, 1058 may have a compliance such that the relative movement of the housing 1052 and/or diaphragm 1056 in response to the external pressure may be coupled to the piezoelectric material or membrane 1062, sometimes through a mechanical linkage or arm 1060. In FIG. 12, the piezoelectric membrane 1062 is shown mechanically coupled to the inner diaphragm 1058 via a mechanical linkage or arm 1060. However, it is contemplated that the piezoelectric material or membrane 1062 may be adhered directly to the inner diaphragm 1058, or the inner diaphragm 1058 may be made from or otherwise form the piezoelectric material or membrane 1062.

As the diaphragm 1056 flexes in response the external pressure 1070, force is transferred 1072 through the fluid filled cavity 1064 to the inner diaphragm 1058. The inner diaphragm 1058 then transfers the force to the piezoelectric material or membrane 1062, sometimes through a mechanical linkage or arm 1060. The force applied to the piezoelectric membrane 1062 generates an voltage (and/or s current). The voltage (and/or current) may be transferred via one or more electrical conductors 1074 to the electrical circuitry of the LCP 1050 where it is converted from a voltage (and/or a current) to a pressure reading.

In some cases, the one or more electrical conductors 1024 may include a first electrical conductor coupled to a first side of the piezoelectric membrane 1062 and a second electrical conductor coupled a second side, opposite of the first side of the piezoelectric membrane 1062, such that the voltage (and/or current) generated across the piezoelectric membrane 1062 is transmitted to the electrical circuitry. In some instances, the electrical conductors may be coupled to first and second pressure sensor electrodes positioned on opposite sides of the piezoelectric membrane 1062.

The voltage generated by the piezoelectric material may be calibrated relative to external pressures applied prior to implantation of the LCP 1050 in a patient. The calibration data may be stored in the memory and/or electrical circuitry of the LCP 1050. In some cases, there may be some pressure loss (e.g., in the range of 1-20% or more) between the pressure exerted on the housing 1052 and the pressure applied to the piezoelectric membrane 1062. This pressure loss may be compensated for (e.g., nullified) by adjusting the algorithm that converts the voltage (and/or current) generated by the piezoelectric material to a pressure using the calibration data stored in the LCP 1050.

In the example of FIG. 12, the battery 1076 is shown adjacent the piezoelectric membrane 1062. However, many different configurations of the internal components of the LCP 1050 are contemplated. In the example shown, the processing module (e.g., circuitry or control electronics) may be positioned in a distal portion of the housing 1052 adjacent to the distal electrode. The one or more electrical conductors 1074 may be formed of a polyimide or similar interconnect having a cross-sectional dimension in the range of less than 250 microns. It is contemplated that the inside surface of the housing 1052 may be electrically insulated and the electrical conductors 1074 (e.g., trace) may be positioned on the inside surface of the housing 1052 or along the outer surface of the battery 1076, as desired. Alternatively, wires or a ribbon cable may be used. These are just examples.

Figure 13:
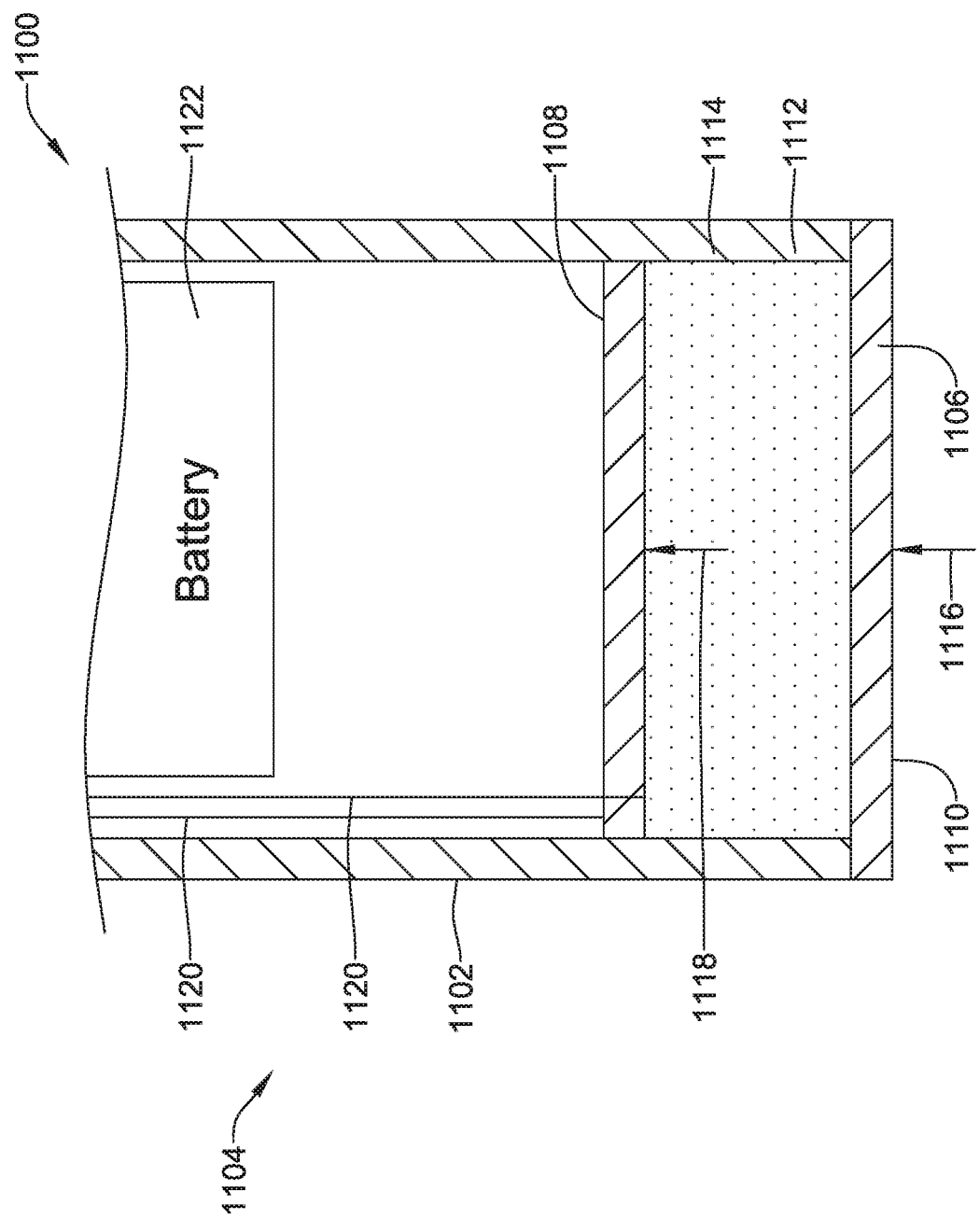
FIG. 13 is a schematic cross-sectional view of a proximal end portion of another illustrative LCP.

FIG. 13 illustrates a proximal end portion 1104 of another illustrative LCP 1100 having a diaphragm 1106 and a piezoelectric membrane 1108. The LCP 1100 may be similar in form and function to the LCPs 100, 610, 900 described above. The LCP 1100 may include any of the modules and/or structural features described above with respect to the LCPs 100, 610, 900.

The LCP 1100 may include a shell or housing 1102 having a proximal end portion 1104 and a distal end (not explicitly shown). The housing 1102 may include a proximal end surface 1110 facing proximally (e.g., in a generally opposite direction from the distal end surface). In some instances, the proximal end surface 1110 of the housing 1102 may form a diaphragm 1106. In some cases, the diaphragm 1106 may be formed from the housing material itself, but this is not required. When so provided, the wall thickness of the housing in the region of the diaphragm 1106 may be thinned to increase the flexibility of the diaphragm 1106, although this is not required. In some cases, the diaphragm 1106 may be formed from another material, such as but not limited to titanium, titanium foil, silicone, polyimides, etc. to form a deformable or movable diaphragm 1106 that is responsive to a desired pressure range applied to the diaphragm 1106.

The diaphragm 1106 may flex or deform to transfer a pressure external to the housing 1102 to a layer of piezoelectric material or a piezoelectric membrane 1108 located within the housing 1102. In some embodiments, a cavity 1112 filled with a fluid 1114 may be positioned between the diaphragm 1106 and the piezoelectric membrane 1108. The fluid filled cavity 1112 is shown in fluid communication with the diaphragm 1106 such that the fluid filled cavity 1112 may communicate a measure related to the pressure 1116 applied by the environment to the piezoelectric membrane 1108. The fluid filled cavity 1112 may be filled with an incompressible fluid 1114. In some cases, the fluid filled cavity 1112 may be filled with a non-conductive fluid 1114. In some cases, the fluid 1114 may be highly soluble to gases that may be inside of the housing, particularly at body temperature (e.g., 37° C.). For example, the fluid 1114 may be highly soluble to hydrogen, helium, nitrogen, argon, water, and/or other gases or liquids that might arise inside of the housing as a result of, for example, outgassing of internal components of the LCP 1100.

The diaphragm 1106 may have a compliance such that the relative movement of the housing 1102 and/or diaphragm 1106 in response to a desired range of external pressures is coupled 1118 to the piezoelectric material or membrane 1108 though the fluid 1114. The force 1118 applied to the piezoelectric membrane 1108 may generate a voltage (and/or a current). The voltage (and/or current) may be transferred via one or more electrical conductors 1120 to the electrical circuitry of the LCP 1100 where it may be converted from a voltage (and/or current) to a pressure reading. It is contemplated that in some instances, the piezoelectric membrane 1108 may be formed from a piezoelectric material or have a piezoelectric material formed on a surface of another flexible material as described with respect to, for example, FIG. 10.

In some cases, the one or more electrical conductors 1120 may include a first electrical conductor coupled to a first side of the piezoelectric membrane 1108 and a second electrical conductor coupled a second side, opposite of the first side of the piezoelectric membrane 1108, such that the voltage (and/or current) generated by the piezoelectric material or membrane 1108 is transmitted to the electrical circuitry. In some instances, the electrical conductors may be coupled to first and second pressure sensor electrodes positioned on opposite sides of the piezoelectric membrane 1108.

The voltage (and/or current) generated by piezoelectric membrane 1108 may be calibrated relative to external pressures applied prior to implantation of the LCP 1100 in a patient. The calibration data may be stored in the memory and/or electrical circuitry of the LCP 1100. In some cases, there may be some pressure loss (e.g., in the range of 1-20% or more) between the pressure exerted on the housing 1102 and the pressure applied to the piezoelectric membrane 1108. This pressure loss may be compensated for (e.g., nullified) by adjusting the algorithm that converts the voltage (and/or current) generated by the piezoelectric membrane 1108 to a pressure using the calibration data stored in the LCP 1100.

In the example of FIG. 13, the battery 1122 is shown adjacent the piezoelectric membrane 1108. However, many different configurations of the internal components of the LCP 1100 are contemplated. In the example shown, the processing module (e.g., circuitry or control electronics) may be positioned in a distal portion of the housing 1102 adjacent to the distal electrode. The one or more electrical conductors 1120 may be formed of a polyimide or similar interconnect having a cross-sectional dimension in the range of less than 250 microns. It is contemplated that the inside surface of the housing 1102 may be electrically insulated and the electrical conductors 1120 (e.g., trace) may be positioned on the inside surface of the housing 1102 or along the outer surface of the battery 1122, as desired. Alternatively, wires or a ribbon cable may be used. These are just examples.

Figure 14:
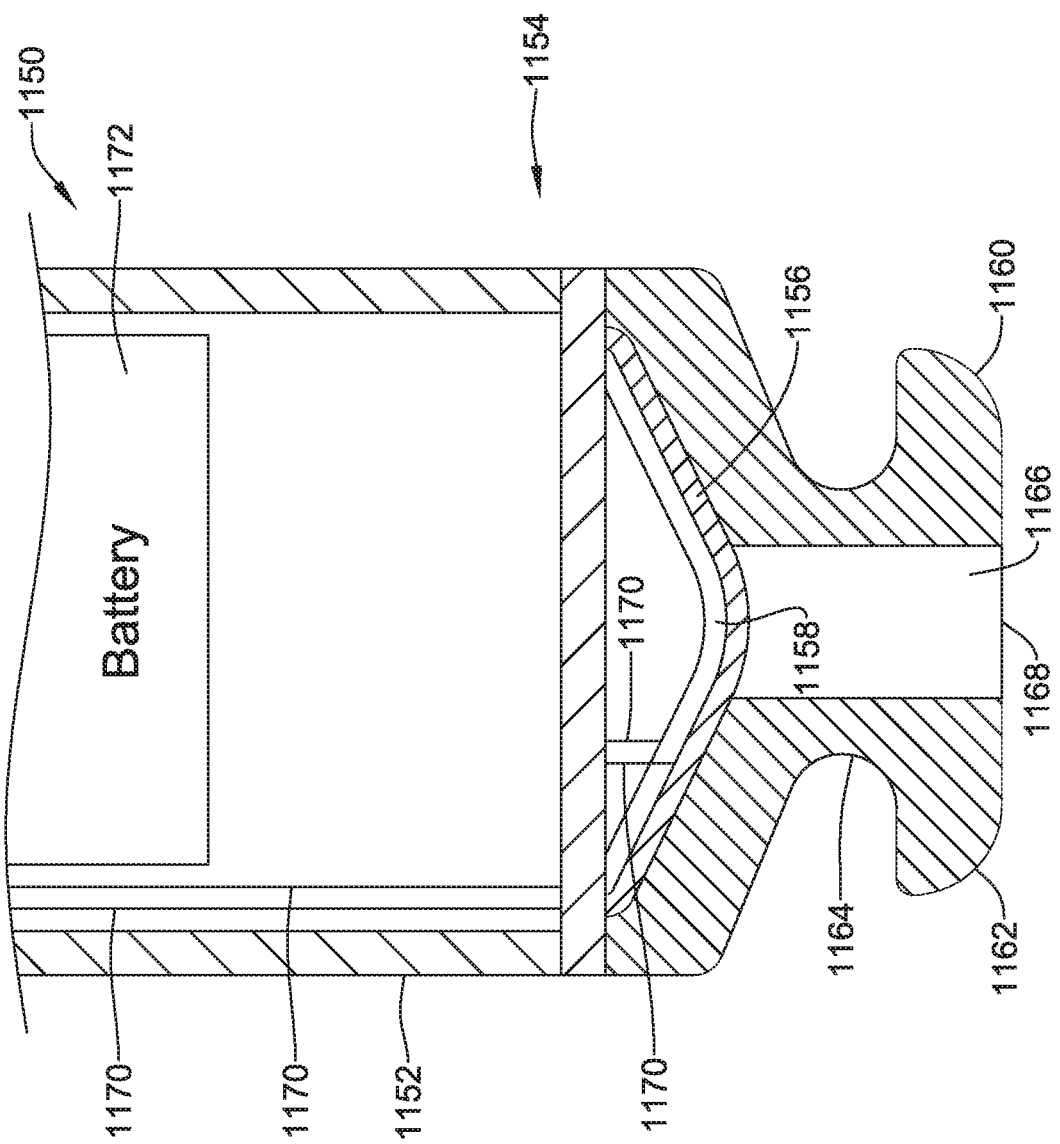
FIG. 14 is a schematic cross-sectional view of a proximal end portion of another illustrative LCP.

FIG. 14 illustrates a cross-sectional view of a proximal end portion 1154 of another illustrative LCP 1150 having a diaphragm 1156 and piezoelectric membrane 1158. The LCP 1150 may be similar in form and function to the LCPs 100, 610, 900 described above. The LCP 1150 may include any of the modules and/or structural features described above with respect to the LCPs 100, 610, 900.

The LCP 1150 may include a shell or housing 1152 having a proximal end portion 1154 and a distal end (not explicitly shown). In this example, the housing 1152 includes a docking member 1160 extending proximally from the proximal end portion 1154. The docking member 1160 may be configured to facilitate delivery and/or retrieval of the LCP 1150. For example, the docking member 1160 may extend from the proximal end portion 1154 of the housing 1152 along a longitudinal axis of the housing 1152. The docking member 1160 may include a head portion 1162 and a neck portion 1164 extending between the housing 1152 and the head portion 1162. The head portion 1162 may be an enlarged portion relative to the neck portion 1164. An access port 1166 may extend through the head portion 1162 and the neck portion 1164 to fluidly couple the diaphragm 1156 with the blood in the heart. The diaphragm 1156 may be constructed using any of the materials and/or configurations described herein. In some cases, the diaphragm 1156 may be positioned at the proximal opening 1168 of the access port 1166.

It is contemplated that the docking member 1160 may be formed as a separate structure from the housing 1152 and subsequently attached to the housing 1152. For example, the docking member 1160 may be 3-D metal structure that is welded (or otherwise coupled or secured) to the housing 1152. In other embodiments, the docking member 1160 and the housing 1152 may be formed as a single monolithic structure.

A piezoelectric membrane 1158 may be positioned adjacent to, but not necessarily in direct contact with the diaphragm 1156. In some cases, the piezoelectric membrane 1158 may be positioned directly on an inner surface of the diaphragm 1156, such as described with respect to FIG. 10. In other embodiments, the piezoelectric membrane 1158 may be mechanically and/or fluidly coupled to the diaphragm 1156 through a mechanical linkage and/or a fluid filled chamber, similar to that described above. As the diaphragm 1156 flexes in response the an external pressure, the piezoelectric membrane 1158 may also flex. The stress on the piezoelectric membrane 1158 may generate a voltage (and/or current). The voltage (and/or current) may be transferred via one or more electrical conductors 1170 to the electrical circuitry of the LCP 1150 where it is converted from a voltage (and/or current) to a pressure reading. In some embodiments, the piezoelectric membrane 1158 may be operatively connected to the housing 1152 which in turn is operatively coupled to the circuitry or control electronics.

In some cases, the one or more electrical conductors 1170 may include a first electrical conductor coupled to a first side of the piezoelectric membrane 1158 and a second electrical conductor coupled a second side, opposite of the first side of the piezoelectric membrane 1158, such that the voltage (and/or current) generated across the piezoelectric membrane 1158 is transmitted to the electrical circuitry. In some instances, the electrical conductors may be coupled to first and second pressure sensor electrodes positioned on opposite sides of the piezoelectric membrane 1158.

FIG. 14 illustrates the battery 1172 adjacent to the piezoelectric membrane 1158. However, many different configurations of the internal components of the LCP 1150 are contemplated. The one or more electrical conductors 1170 may be formed of a polyimide or similar interconnect having a cross-sectional dimension in the range of less than 250 microns. It is contemplated that the inside surface of the housing 1152 may be electrically insulated and the electrical conductors 1170 (e.g., trace) positioned on the inside surface of the housing 1152 or along the outer surface of the battery 1172, as desired. Alternatively, wires or a ribbon cable may be used. These are just examples.

Figure 15:
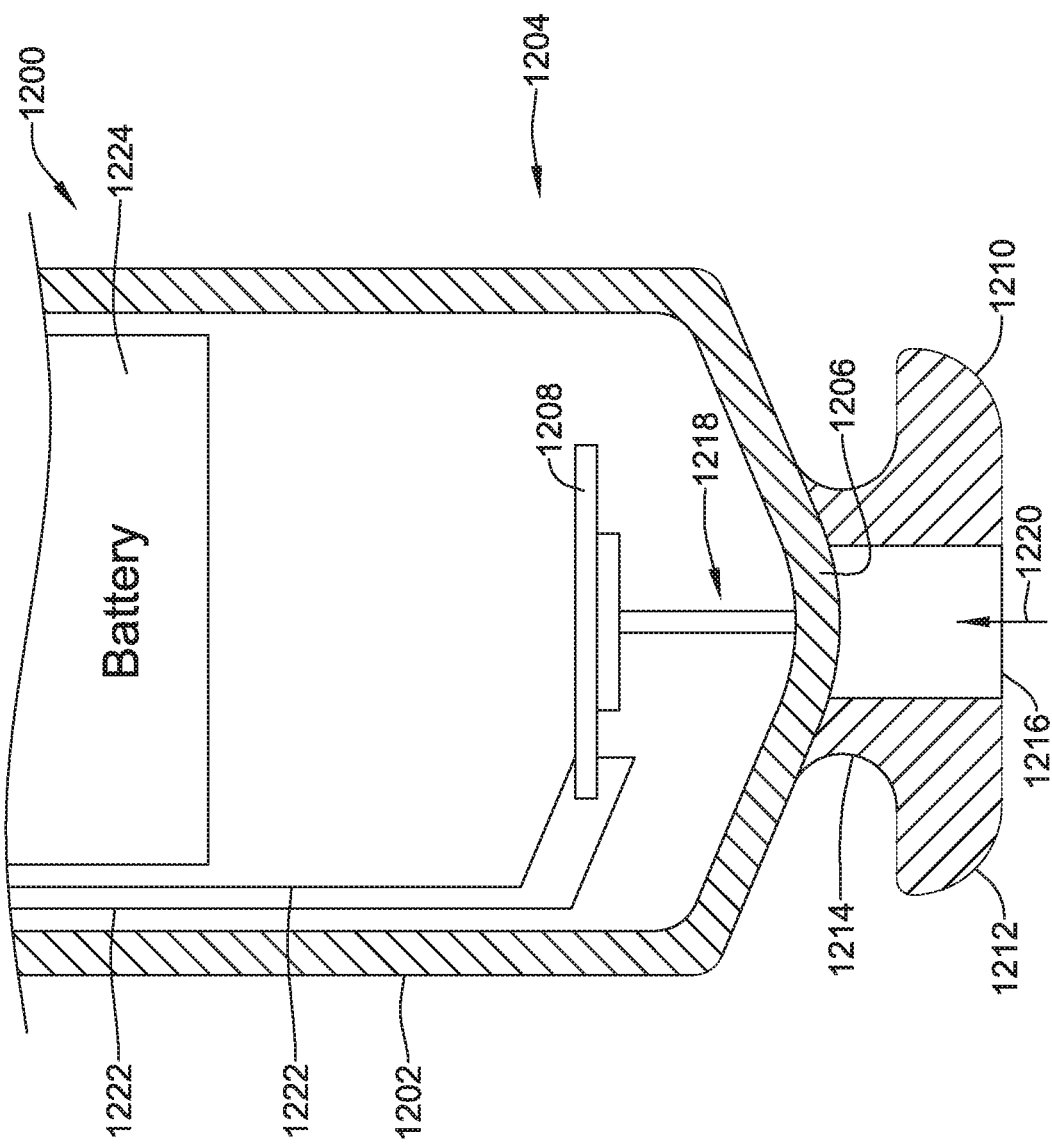
FIG. 15 is a schematic cross-sectional view of a proximal end of another illustrative LCP.

FIG. 15 illustrates a cross-sectional view of a proximal end portion 1204 of another illustrative LCP 1200 having a diaphragm 1206 and a piezoelectric membrane 1208. The LCP 1200 may be similar in form and function to the LCPs 100, 610, 900 described above. The LCP 1200 may include any of the modules and/or structural features described above with respect to the LCPs 100, 610, 900.

The LCP 1200 may include a shell or housing 1202 having a proximal end portion 1204 and a distal end (not explicitly shown). The housing 1202 may include a docking member 1210 extending proximally from the proximal end portion 1204. The docking member 1210 may be configured to facilitate delivery and/or retrieval of the LCP 1200. For example, the docking member 1210 may extend from the proximal end portion 1204 of the housing 1202 along a longitudinal axis of the housing 1202. The docking member 1210 may include a head portion 1212 and a neck portion 1214 extending between the housing 1202 and the head portion 1212. The head portion 1212 may be an enlarged portion relative to the neck portion 1214. An access port 1216 may extend through the head portion 1212 and the neck portion 1214 to fluidly couple the diaphragm 1206 with the blood in the heart. The diaphragm 1206 may be constructed using any of the materials and/or configurations described herein. In some cases, the diaphragm 1206 may be positioned at the proximal opening 1168 of the access port 1216.

It is contemplated that the docking member 1210 may be formed as a separate structure from the housing 1202 and subsequently attached to the housing 1202. For example, the docking member 1210 may be 3-D metal structure that is welded (or otherwise coupled or secured) to the housing 1202. In other embodiments, the docking member 1210 and the housing 1202 may be formed as a single monolithic structure.

A piezoelectric membrane 1208 may be positioned adjacent to, but not necessarily in direct contact with the diaphragm 1206. In some embodiments, the piezoelectric membrane 1208 may be coupled to the diaphragm 1206 via a mechanical linkage or arm 1218. At least part of the piezoelectric membrane 1208 may be held in place relative to the housing 1202 such that movement of the diaphragm 1206 and mechanical linkage or arm 1218 relative to the piezoelectric membrane 1208 induces a stress in the piezoelectric membrane 1208. As the diaphragm 1206 flexes in response the external pressure 1220, the linkage 1218 moves and transfers the force to the piezoelectric membrane 1208. The force applied to the piezoelectric membrane 1208 generates a voltage (and/or current). The voltage (and/or current) may be transferred via one or more electrical conductors 1222 to the electrical circuitry of the LCP 1000 where it is converted from a voltage (and/or current) to a pressure reading.

In some cases, the one or more electrical conductors 1222 may include a first electrical conductor coupled to a first side of the piezoelectric membrane 1208 and a second electrical conductor coupled a second opposite side of the piezoelectric membrane 1208 such that the voltage (and/or current) generated across the piezoelectric membrane 1208 is transmitted to the electrical circuitry. In some instances, the electrical conductors may be coupled to first and second pressure sensor electrodes positioned on opposite sides of the piezoelectric membrane 1208.

FIG. 15 illustrates the battery 1224 adjacent to the piezoelectric membrane 1208. However, many different configurations of the internal components of the LCP 1200 are contemplated. The one or more electrical conductors 1222 may be formed of a polyimide or similar interconnect having a cross-sectional dimension in the range of less than 250 microns. It is contemplated that the inside surface of the housing 1202 may be electrically insulated and the electrical conductors 1222 (e.g., trace) positioned on the inside surface of the housing 1202 or along the outer surface of the battery 1224, as desired. Alternatively, wires or a ribbon cable may be used. These are just examples.

It is contemplated that any of the embodiments described herein may be modified to include a plurality (e.g., two or more) diaphragms and/or piezoelectric membranes to improve the sensitivity of the pressure readings. For example, it may be desirable for the diaphragm(s) to have the largest surface area possible. This may be accomplished through a single, large diaphragm or a plurality of smaller diaphragms. It should also be understood that the placement of the diaphragm and/or piezoelectric membrane is not limited to the proximal end region of the LCP. In some cases, the diaphragm and/or piezoelectric membrane may be positioned in or adjacent to a sidewall and/or near the distal end region.

In some cases, the diaphragms and/or piezoelectric membranes may include contours configured to increase the sensitivity and/or linearity of the diaphragms and/or piezoelectric membranes. Some illustrative contours may include, but are not limited to, a concave surface, a convex surface, an undulating surface, a generally convex surface having a generally concave central region, etc. It is contemplated that the contours may be tuned for the application and/or placement of the device.

Regardless of the placement location of the LCP, some static pressure may be applied to the diaphragm and/or piezoelectric membrane upon implantation of the device. This may cause the diaphragm and/or piezoelectric membrane to flex from its un-implanted configuration. The LCP may be configured to detect changes in pressure over time which are indicated by a movement of the diaphragm. As such, and in some cases, it may be desirable to pre-tune the diaphragm and/or piezoelectric membrane to optimize the pressure range of the diaphragm and/or piezoelectric membrane when the LCP is implanted. This may be accomplished by deforming the diaphragm and/or piezoelectric membrane during manufacture in a direction opposite to the static pressure exerted by the chamber of the heart such that the diaphragm and/or piezoelectric membrane are in a neutral configuration after implantation (as opposed to flexed inwards under the static pressure of the implantation chamber).

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A leadless cardiac pacemaker (LCP) for implantation in a ventricle of a heart, wherein the heart includes an atrium that contracts to supply blood to the ventricle, the LCP configured to sense cardiac activity and to deliver pacing therapy to the ventricle of the heart, the LCP comprising:
   a housing having a proximal end and a distal end;
   a first electrode secured relative to the housing and exposed to the environment outside of the housing;
   a second electrode secured relative to the housing and exposed to the environment outside of the housing;
   a diaphragm that is exposed to the environment outside of the housing, the diaphragm is responsive to an external pressure applied to the diaphragm by the environment outside of the housing;
   a piezoelectric membrane having a first pressure sensor electrode and a second pressure sensor electrode, the piezoelectric membrane is configured to generate an electrical voltage between the first pressure sensor electrode and the second pressure sensor electrode in response to a flexing of the diaphragm caused by a pressure change applied to the diaphragm;
   circuitry in the housing operatively coupled to the first electrode and the second electrode of the LCP, and also operatively coupled to the first pressure sensor electrode and the second pressure sensor electrode, the circuitry is configured to deliver a pacing therapy to the ventricle of the heart via the first electrode and the second electrode;
   wherein the diaphragm is configured to flex and cause the piezoelectric membrane to generate an electrical signal responsive to a change in pressure in the ventricle of the heart that is caused by a contraction of the atrium of the heart, and wherein the circuitry is configured to identify an atrial contraction of the heart based at least in part on the electrical signal produced by the piezoelectric membrane responsive to a change in pressure in the ventricle of the heart that is caused by a contraction of the atrium of the heart; and
   wherein a timing of delivery of at least part of the pacing therapy delivered to the ventricle of the heart by the circuitry is based at least in part on the identified atrial contraction of the heart.

2. The LCP of claim 1, wherein the circuitry is configured to detect a pressure pulse that corresponds to an atrial kick by monitoring the electrical voltage generated between the first pressure sensor electrode and the second pressure sensor electrode by the piezoelectric membrane.

3. The LCP of claim 1, wherein the diaphragm has an interior surface that faces toward an interior of the housing, and the piezoelectric membrane is secured to at least part of the interior surface of the diaphragm.

4. The LCP of claim 1, wherein the diaphragm has an interior surface that faces toward an interior of the housing, and the piezoelectric membrane is spaced a distance from the interior surface of the diaphragm and is operatively coupled to the interior surface of the diaphragm via an incompressible fluid.

5. The LCP of claim 4, wherein the incompressible fluid is in a fluid cavity that is at least partially defined by the interior surface of the diaphragm and is in operative communication with both the interior surface of the diaphragm and the piezoelectric membrane, wherein the fluid cavity is configured to communicate a pressure applied to the incompressible fluid by the diaphragm to the piezoelectric membrane.

6. The LCP of claim 1, wherein the diaphragm has an interior surface that faces toward an interior of the housing, and the piezoelectric membrane is spaced a distance from the interior surface of the diaphragm and is operatively coupled to the interior surface of the diaphragm via a mechanical linkage, wherein the mechanical linkage is configured to translate movement of the diaphragm to a pressure applied to the piezoelectric membrane.

7. The LCP of claim 1, wherein the diaphragm of the housing includes one or more contours.

8. The LCP of claim 1, wherein the diaphragm has a thinness that produces a flexibility in the diaphragm that is responsive to a change in pressure in the ventricle of the heart that is caused by the contraction of the atrium of the heart and causes the piezoelectric membrane to generate the electrical signal that is suitable for the circuitry to identify the atrial contraction of the heart.

9. The LCP of claim 1, wherein the diaphragm is structured and is formed of a material that produces a flexibility in the diaphragm that is responsive to a change in pressure in the ventricle of the heart that is caused by the contraction of the atrium of the heart and causes the piezoelectric membrane to generate the electrical signal that is suitable for the circuitry to identify the atrial contraction of the heart.

10. The LCP of claim 1, wherein the diaphragm is integrally formed with the housing.

11. The LCP of claim 1, wherein the diaphragm is hermetically sealed to the housing.

12. The LCP of claim 1, further comprising a fixation member at the distal end of the housing for fixing the distal end of the housing to an implant site, and wherein the diaphragm of the housing is adjacent the proximal end of the housing.

13. The LCP of claim 1, wherein the housing includes an elongated body with a distal end surface facing distally and a proximal end surface facing proximally, wherein the diaphragm of the housing is situated on the proximal end surface of the housing.

14. The LCP of claim 1, wherein the circuitry is configured to sample the electrical signal produced by the piezoelectric membrane at a sample rate of 100 Hertz or more.

15. A leadless cardiac pacemaker (LCP) for implantation in a ventricle of a heart, wherein the heart includes an atrium that contracts to supply blood to the ventricle, the LCP configured to sense cardiac activity and to pace the heart, the LCP comprising:
   a housing having a proximal end and a distal end;
   a first electrode secured relative to the housing and exposed to the environment outside of the housing;
   a second electrode secured relative to the housing and exposed to the environment outside of the housing;
   the housing having a diaphragm that is exposed to the environment outside of the housing, the diaphragm is responsive to a pressure applied to the diaphragm by the environment outside of the housing;

a piezoelectric material operatively coupled to the diaphragm of the housing for detecting a deflection in the diaphragm by generating charge that is representative of the pressure applied to the diaphragm by the environment outside of the housing; and circuitry in the housing in operative communication with the first electrode, the second electrode and the piezoelectric material, the circuitry is configured to deliver a pacing therapy to the patient's heart via the first electrode and the second electrode, wherein the diaphragm, the piezoelectric membrane and the circuitry are collectively configured to be responsive to a change in pressure in the ventricle of the heart that is caused by a contraction of the atrium of the heart such that the circuitry can identify an atrial contraction of the heart based at least in part on the charge generated by the piezoelectric membrane in response to the change in pressure in the ventricle of the heart that is caused by the contraction of the atrium of the heart;

wherein the circuitry is further configured to control the pacing therapy based, at least in part, on the identified atrial contraction of the heart.

16. The LCP of claim 15, wherein the diaphragm has a thinness that produces a flexibility in the diaphragm that is responsive to a change in pressure in the ventricle of the heart that is caused by the contraction of the atrium of the heart and causes the piezoelectric membrane to generate the charge that is suitable for the circuitry to identify the atrial contraction of the heart.

17. The LCP of claim 15, wherein the diaphragm is structured and is formed of a material that produces a flexibility in the diaphragm that is responsive to a change in pressure in the ventricle of the heart that is caused by the contraction of the atrium of the heart and causes the piezoelectric membrane to generate the charge that is suitable for the circuitry to identify the atrial contraction of the heart.

18. The LCP of claim 17 wherein the circuitry is configured to sample the charge generated by the piezoelectric material at a sample rate of 100 Hertz or more.

19. A leadless cardiac pacemaker (LCP) for implantation in a ventricle of a heart, wherein the heart includes an atrium that contracts to supply blood to the ventricle, the LCP comprising:

a housing having a proximal end and a distal end;

a first electrode secured relative to the housing and exposed to the environment outside of the housing;

a second electrode secured relative to the housing and exposed to the environment outside of the housing;

the housing having a diaphragm that is exposed to the environment outside of the housing, the diaphragm is responsive to a pressure applied to the diaphragm by the environment outside of the housing;

a piezoelectric membrane disposed on an inner surface of the diaphragm, the piezoelectric membrane generating a charge in response to the pressure applied to the diaphragm by the environment outside of the housing, wherein the diaphragm and the piezoelectric membrane are configured to deform with a changing pressure to detect a change in pressure in the ventricle of the heart caused by a contraction of the atrium of the heart; and circuitry in the housing in operative communication with the first electrode, the second electrode and the piezoelectric membrane, wherein the circuitry is configured to detect the change in pressure in the ventricle of the patient's heart caused by the contraction of the atrium from the charge generated by the piezoelectric membrane and/or a change in pressure caused by a heart sound, the circuitry is further configured to deliver an electrostimulation therapy to the patient's heart via the first electrode and the second electrode that is based, at least in part, on the detected change in pressure in the ventricle of the patient's heart caused by the contraction of the atrium.

20. The LCP of claim 19, wherein the piezoelectric membrane comprises polyvinylidene fluoride (PVDF).

21. The LCP of claim 19, wherein the circuitry is configured to sample the charge generated by the piezoelectric membrane at a sample rate of 100 Hertz or more.

* * * * *